(12) United States Patent
Worley et al.

(10) Patent No.: US 8,496,920 B2
(45) Date of Patent: Jul. 30, 2013

(54) N-HALAMINE ACRYLAMIDE MONOMERS AND COPOLYMERS THEREOF FOR BIOCIDAL COATINGS

(75) Inventors: Shelby D. Worley, Auburn, AL (US); Royall M. Broughton, Opelika, AL (US); Hasan B. Kocer, Bursa (TR); Idris Cerkez, Auburn, AL (US)

(73) Assignee: Auburn University, Auburn, AL (US)

( * ) Notice: Subject to any disclaimer, the term of this patent is extended or adjusted under 35 U.S.C. 154(b) by 56 days.

(21) Appl. No.: 13/270,446

(22) Filed: Oct. 11, 2011

(65) Prior Publication Data

US 2012/0183494 A1 Jul. 19, 2012

Related U.S. Application Data

(60) Provisional application No. 61/432,415, filed on Jan. 13, 2011.

(51) Int. Cl.
| | |
|---|---|
| *A01N 43/50* | (2006.01) |
| *A01P 15/00* | (2006.01) |
| *A01P 3/00* | (2006.01) |
| *C08F 8/06* | (2006.01) |
| *C09D 135/00* | (2006.01) |
| *C08B 15/00* | (2006.01) |
| *C07F 7/02* | (2006.01) |
| *C07C 14/00* | (2006.01) |
| *C04B 33/24* | (2006.01) |
| *C04B 35/00* | (2006.01) |
| *B32B 17/10* | (2006.01) |
| *C07D 233/76* | (2006.01) |

(52) U.S. Cl.
USPC ....... 424/78.37; 427/337; 427/341; 428/35.7; 428/441; 428/451; 428/473; 428/500; 514/389; 524/516; 525/281; 525/326.7; 525/356; 548/110; 548/319.5

(58) Field of Classification Search
None
See application file for complete search history.

(56) References Cited

U.S. PATENT DOCUMENTS

| | | | |
|---|---|---|---|
| 3,374,242 A | 3/1968 | Kelley et al. | |
| 6,294,185 B1 * | 9/2001 | Worley et al. | 424/405 |

FOREIGN PATENT DOCUMENTS

WO WO 2012/096694 7/2012

OTHER PUBLICATIONS

International Search Report and Written Opinion dated May 1, 2012 for pending counterpart PCT International Patent Application No. PCT/US11/55717, pp. 1-15.
Liu et al., "Biocidal Acyclic Halamine Polymers: Conversion of Acrylamide-Grafted-Cotton to Acyclic Halamine," Journals of Applied Polymer Science, 2008, vol. 108, pp. 3480-3486.

* cited by examiner

*Primary Examiner* — Kamal Saeed
(74) *Attorney, Agent, or Firm* — Ian J. Griswold; Jason M. Pass; Johnson, Marcou & Isaacs, LLC

(57) ABSTRACT

Novel acrylamide and methacrylamide hydantoin monomers which can be reacted with other acrylamide, methacrylamide, acrylate, and methacrylate monomers to form copolymers, which upon halogenation, provide oxidative coatings which are biocidal for use with various materials including, but not limited to, textiles, filters, and latex paints.

44 Claims, 1 Drawing Sheet

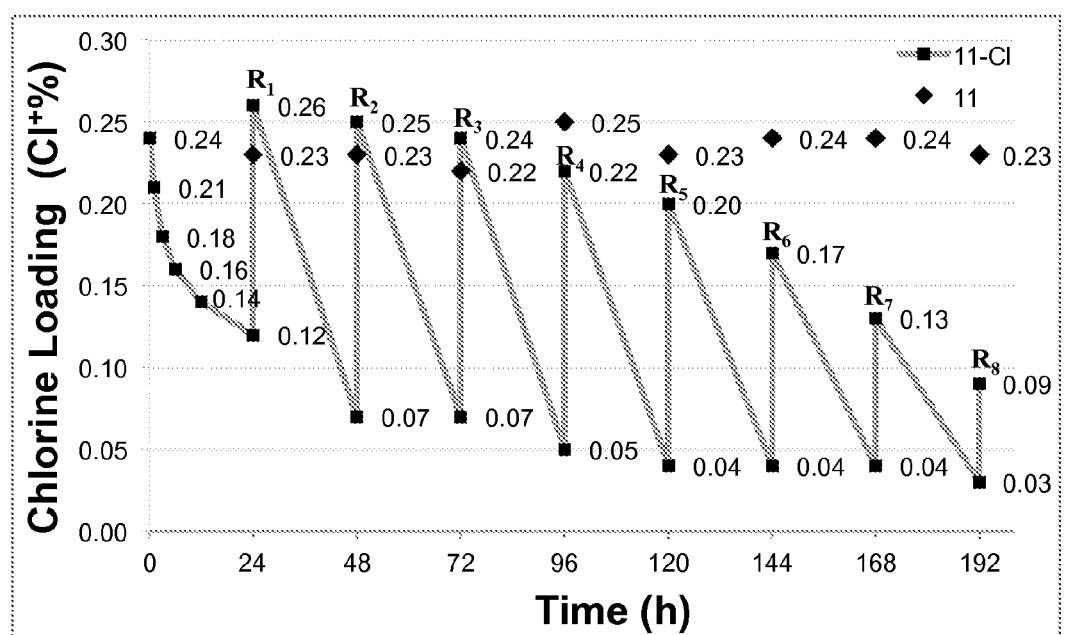
Stability toward repeated UVA light exposure of cotton coated with 11-Cl. ($Cl^+$% remaining).

N-HALAMINE ACRYLAMIDE MONOMERS AND COPOLYMERS THEREOF FOR BIOCIDAL COATINGS

CROSS REFERENCE TO RELATED APPLICATIONS

This application claims the benefit of U.S. Provisional Application Ser. No. 61/432,415 filed Jan. 13, 2011 incorporated herein by reference in its entirety for all of its teachings.

TECHNICAL FIELD OF THE INVENTION

The present invention relates generally to biocidal compositions. More particularly, the present invention relates to novel acrylamide and methacrylamide hydantoin monomers which can be reacted with other acrylamide, methacrylamide, acrylate, and methacrylate monomers to form copolymers, which upon halogenation, provide oxidative coatings which are biocidal for use with various materials including, but not limited to, textiles, filters, and latex paints.

BACKGROUND

Research and development work in the laboratories of Worley and co-workers has proceeded with the goal of producing novel biocidal compounds (for example, see review articles Worley, S. D., Williams, D. E., "Halamine Water Disinfectants", CRC Crit. Rev. Environm. Cntrl. 1988, 18, 133; Worley, S. D., Sun, G., "Biocidal Polymers", Trends Polym. Sci. 1996, 4, 364; Kenawy, E., Worley, S. D., Broughton, R. M., "The Chemistry and Applications of Biocidal Polymers, A State of the Art Review", Biomacromolecules 2007, 8, 1359, and the references incorporated therein). All of the work has focused upon a class of compounds known as organic N-halamines, which are generally heterocyclic monomers or polymers containing nitrogen-halogen bonds. The most stable of these compounds with regard to the release of bleaching free halogen in aqueous solution are those containing N—Cl covalent bonds stabilized by electron-donating substituents, e.g. alkyl groups, such as methyl groups, attached to the carbon atoms in the structures directly linked to the nitrogen atom containing the chlorine atom. The mechanism by which these N-halamine compounds inactivate pathogenic microorganisms is through direct contact in which the N-halamine donates its halogen atom to the biological cell, wherein the cell is inactivated through an oxidation process. If the N—Cl bond on the N-chloramine is sufficiently strong, the disinfection process will be slower than for "free chlorine", the antibacterial agent which is present in household bleach. However, if free chlorine is not appreciably released from an N-chloramine into aqueous media, then undesirable chemical processes, such as corrosion and bleaching, will be minimized.

There is a need for new N-halamine biocidal materials which maintain their disinfection and detoxification properties for long periods of time, load higher amounts of oxidative halogen than those disclosed before, and are resistant to degradation in sunlight. Several N-halamine surface coatings containing hydantoin moieties have been developed; e.g., see U.S. Pat. Nos. 6,969,769 B2; 7,335,373 B2 and 5,882,357 A; these patents, and articles cited above, are hereby incorporated by reference for all of their teachings. However, past biocidal materials developed for surface coatings which contained the hydantoin moieties have the limitation that the hydantoin moiety is tethered to the surface through the imide nitrogen atom of the hydantoin ring, thereby leaving only the amide nitrogen atom of the hydantoin ring as a binding point for oxidative halogen, which limits the amount of biocidal halogen contained in the material.

SUMMARY OF THE INVENTION

The present invention includes various biocidal compounds and compositions, which can be coated on, attached to, or incorporated in a material so as to control and/or inactivate microorganisms and virus particles. Methods of preparing and using the compounds and compositions are also included.

In one disclosed embodiment, the present invention relates to an acrylamide or methacrylamide hydantoinyl monomer containing three nitrogen atoms capable of covalently binding oxidative chlorine or bromine with the structure:

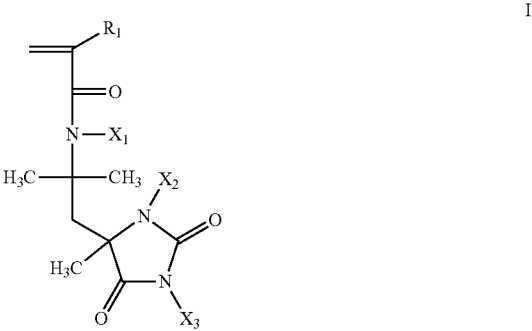

I wherein $R_1$ is H or methyl, and $X_1$, $X_2$, and $X_3$ are independently H, Cl, or Br. A biocidal monomer with the structure above has no more than two of $X_1$, $X_2$, and $X_3$ being H.

Another disclosed embodiment of the present invention relates to a homopolymer comprising the monomer I in the structure above with polymerization occurring through the carbon-carbon double bond, wherein $R_1$ is H or methyl, and $X_1$, $X_2$, and $X_3$ are independently H, Cl, or Br. A biocidal polymer with the structure above has no more than two of $X_1$, $X_2$, and $X_3$ being H.

A further disclosed embodiment of the present invention relates to a random copolymer with the structure:

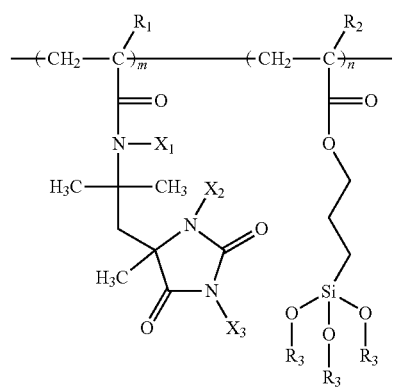

wherein $R_1$ and $R_2$ are independently H or methyl, and $X_1$, $X_2$, and $X_3$ are independently H, Cl, or Br. $R_3$ is H, methyl, or ethyl. The ratios of coefficients m to m+n vary between 0.99 and 0.01, most preferably 0.6 to 0.4. A biocidal copolymer with the above structure has no more than two of $X_1$, $X_2$, and $X_3$ being H.

Another disclosed embodiment of the present invention relates to a random copolymer with the structure:

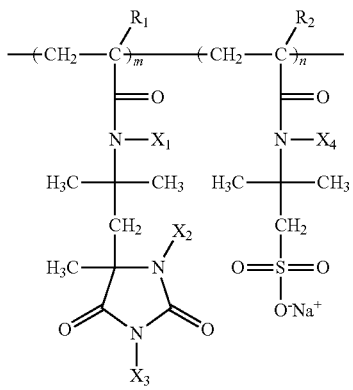

wherein $R_1$ and $R_2$ are independently H or methyl, and $X_1$, $X_2$, $X_3$, and $X_4$ are independently H, Cl, or Br. The ratios of coefficients m to m+n vary between 0.99 and 0.01, most preferably 0.8 to 0.7. A biocidal copolymer with the above structure has no more than three of $X_1$, $X_2$, $X_3$, and $X_4$ being H.

Another disclosed embodiment of the present invention relates to a random copolymer with the structure:

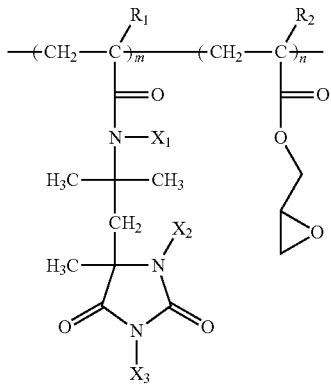

wherein $R_1$ and $R_2$ are independently H or methyl, and $X_1$, $X_2$, and $X_3$ are independently H, Cl, or Br. The ratios of coefficients m to m+n vary between 0.99 and 0.01, most preferably 0.6 to 0.4. A biocidal copolymer with the above structure has no more than two of $X_1$, $X_2$, and $X_3$ being H.

Yet another disclosed embodiment of the present invention relates to a random copolymer with structure:

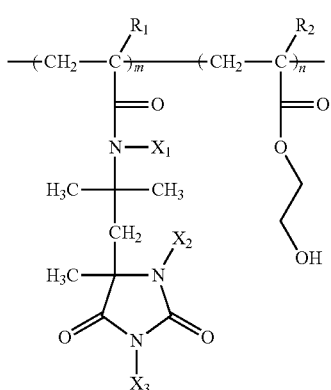

wherein $R_1$ and $R_2$ are independently H or methyl, and $X_1$, $X_2$, and $X_3$ are independently H, Cl, or Br. The ratios of coefficients m to m+n vary between 0.99 and 0.01, most preferably 0.6 to 0.4. A biocidal copolymer with the above structure has no more than two of $X_1$, $X_2$, and $X_3$ being H.

Another disclosed embodiment of the present invention relates to a surface or material to which a precursor acrylamide or methacrylamide hydantoinyl monomer, polymer, or copolymer or halogenated acrylamide or methacrylamide hydantoinyl monomer, polymer, or copolymer has been attached physically or chemically or with which it has been blended.

Still another disclosed embodiment of the present invention relates to a method of rendering a surface or material biocidal by attaching to it physically or chemically through hydroxyl moieties on a siloxane or through epoxide or alcohol moieties or by blending with the monomer, polymer, or copolymer as defined above, wherein at least one of $X_1$, $X_2$, $X_3$, and $X_4$ is Cl or Br.

Another disclosed embodiment of the present invention relates to a method of rendering a surface or material biocidal by attaching to it physically or chemically through hydroxyl moieties on a siloxane or through epoxide or alcohol moieties or by blending with the monomer, polymer, or copolymer as defined above, wherein $X_1$, $X_2$, $X_3$, and $X_4$ are H, and then exposing the thus modified surface or material to a source of oxidative chlorine or bromine.

A further disclosed embodiment of the present invention relates to the synthesis and use of an acrylamide or methacrylamide hydantoinyl monomer, homopolymers, and copolymers which contain two to three amide nitrogen atoms and one imide nitrogen atom which can be reacted with sources of oxidative chlorine or bromine either before or after attachment to a surface or blending with a material, so as to render the surface or material biocidal. The biocidal coatings and materials can be used to inactivate pathogenic microorganisms, such as bacteria, fungi, and yeasts, as well as virus particles, which can cause infectious diseases, and those microorganisms which cause noxious odors and unpleasant coloring, such as mildew. The coatings and blends are compatible with a wide variety of substrates including, but not limited to, cellulose, synthetic fibers, filter materials, latex paint, chitin, chitosan, glass, ceramics, plastics, rubber, cement grout, latex caulk, porcelain, acrylic films, vinyl, polyurethanes, silicon tubing, marble, metal oxides, and silica.

Additional advantages will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary only and are not restrictive.

BRIEF DESCRIPTION OF THE DRAWINGS

FIG. 1 is a graph showing the stabilities of copolymer 11 and the chlorinated copolymer 11 (11-Cl) on cotton toward UVA degradation following a series of rechlorinations.

DETAILED DESCRIPTION OF DISCLOSED EMBODIMENTS

Before the present compounds, compositions, articles, and/or methods are disclosed and described, it is to be understood that the aspects described below are not limited to specific synthetic methods; specific synthetic methods may, of course, vary. It is also to be understood that the terminology used herein is for the purpose of describing particular aspects and is not intended to be limiting.

In this specification, and in the claims that follow, reference will be made to a number of terms, which shall be defined to have the following meanings:

Singular forms like "a", "an", "the", "compound", "monomer", "polymer", and "copolymer" include plural referents unless the context clearly dictates otherwise.

Ranges may be expressed herein as from "about" one particular value and/or to "about" another particular value. When such a range is expressed, another aspect includes from the one particular value and/or to the other particular value.

A weight percent of a component, unless specifically stated to the contrary, is based on the total weight of the formulation or composition in which the component is included.

Variables such as $X_1$, $X_2$, $X_3$, $X_4$, $R_1$, $R_2$, and $R_3$ used throughout the application are the same variables as previously defined unless stated to the contrary.

As used herein, the term "biocidal" means activity that inactivates microorganisms and/or virus particles.

As used herein, the term "halogenated" means that the imide and/or amide nitrogen atoms in a monomer, polymer, or copolymer are covalently bonded to oxidative Cl or Br, that is Cl or Br having a +1 oxidation state.

As used herein, the term "unhalogenated precursor" means that the imide and/or amide nitrogen atoms in a monomer, polymer, or copolymer are covalently bonded to H.

As used herein, the term "DA" refers to 2-acrylamido-2-methyl-4-pentanone.

As used herein, the term "HA" refers to the monomer having the structure:

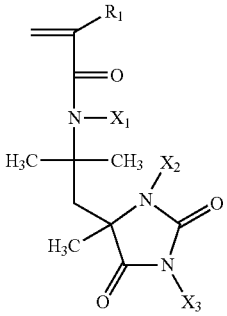

in which $R_1$, $X_1$, $X_2$, and $X_3$ are H.

As used herein, the term "HA-Cl" refers to fully or partially chlorinated "HA".

As used herein, the term "SL" refers to 3-(trimethoxysilyl)propyl methacrylate.

As used herein, the term "HASL" refers to the copolymer having the structure:

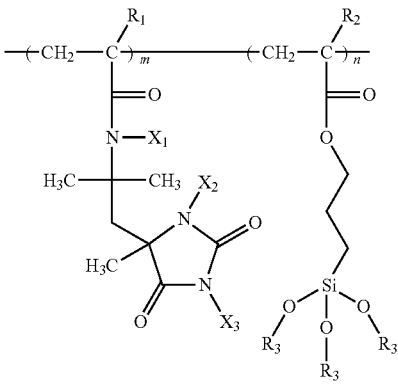

in which $R_1$, $X_1$, $X_2$, and $X_3$ are H, and $R_2$ and $R_3$ are methyl; the ratios of coefficients m to m+n vary between 0.99 and 0.01, most preferably 0.6 to 0.4.

As used herein, the term "SA" refers to 2-acrylamido-2-methyl-1-propanesulfonic acid, sodium salt.

As used herein, the term "HASA" refers to the copolymer having the structure:

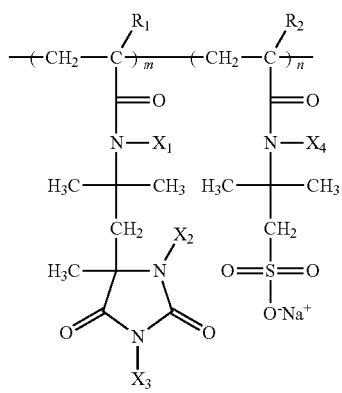

in which $R_1$, $R_2$, $X_1$, $X_2$, $X_3$, and $X_4$ are H; the ratios of coefficients m to m+n vary between 0.99 and 0.01, most preferably 0.8 to 0.7.

As used herein, the term "GM" refers to glycidyl methacrylate.

As used herein, the term "HAGM" refers to the copolymer having the structure:

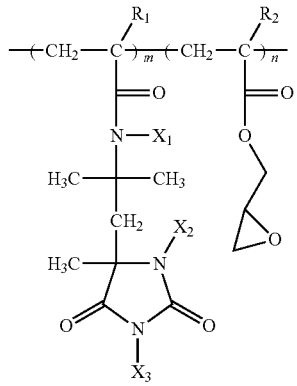

in which $R_1$, $X_1$, $X_2$, and $X_3$ are H, and $R_2$ is methyl; the ratios of coefficients m to m+n vary between 0.99 and 0.01, most preferably 0.6 to 0.4.

As used herein, the term "OH" refers to 2-hydroxyethyl methacrylate.

As used herein, the term "HAOH" refers to the copolymer having the structure:

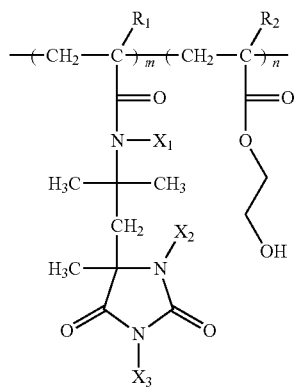

in which $R_1$, $X_1$, $X_2$, and $X_3$ are H, and $R_2$ is methyl; the ratios of coefficients m to m+n vary between 0.99 and 0.01, most preferably 0.6 to 0.4.

The present invention may be understood more readily by reference to the following detailed description of specific embodiments and the examples included therein.

A. Compounds/Compositions

In a disclosed embodiment described herein are compounds having the structure:

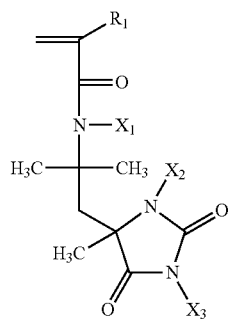

I wherein $R_1$ is H or methyl, and $X_1$, $X_2$, and $X_3$ are H. This unhalogenated monomer compound can be synthesized by a method to be described below. It can be added to a material as a blend or attached to a surface with a grafting procedure. It can be halogenated by exposure to a source of chlorine or bromine before or after it is added to a material as a blend or attached to a surface with a grafting procedure to create a biocidal material or surface. In this event at least one of $X_1$, $X_2$, and $X_3$ is Cl or Br. The presence of the methyl groups adjacent to the nitrogen-halogen functional groups serves to stabilize the structure from loss of oxidative halogen through an inductive electronic effect, steric effects, and prevention of dehydrohalogenation which would occur if one or more H atoms were present adjacent to the nitrogen-halogen functional groups.

In a second disclosed embodiment described herein monomer I above can be polymerized by a method to be described below to form a homopolymer of I. This can be done before or after halogenation with a source of oxidative chlorine or bromine, and before or after blending with a material or attachment to a surface with a grafting procedure to form a biocidal material or surface. In this event at least one of $X_1$, $X_2$, and $X_3$ is Cl or Br.

In a third disclosed embodiment described herein monomer I above can be copolymerized with another monomer possessing a carbon-carbon double bond to create a random copolymer, such as represented by the structure:

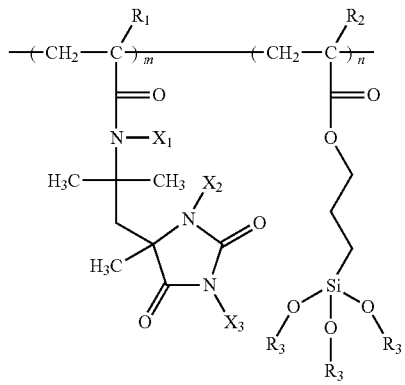

wherein $R_1$ and $R_2$ are independently H or methyl, and $X_1$, $X_2$, and $X_3$ are independently H, Cl, or Br. $R_3$ is H, methyl, or ethyl. The ratios of coefficients m to m+n vary between 0.99 and 0.01, most preferably 0.6 to 0.4. A biocidal copolymer with the structure above has no more than two of $X_1$, $X_2$, and $X_3$ being H. The preparation of this copolymer and its halogenation will be described below.

In a fourth disclosed embodiment described herein monomer I above can be copolymerized with another monomer possessing a carbon-carbon double bond to create a random copolymer, such as represented by the structure:

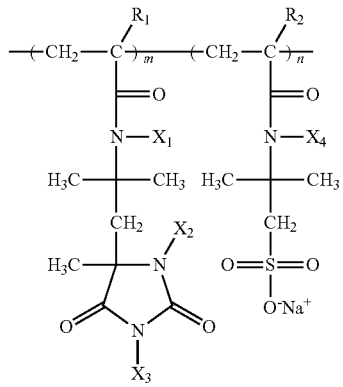

wherein $R_1$ and $R_2$ are independently H or methyl, and $X_1$, $X_2$, $X_3$, and $X_4$ are independently H, Cl, or Br. The ratios of coefficients m to m+n vary between 0.99 and 0.01, most preferably 0.8 to 0.7. A biocidal copolymer with the structure above has no more than three of $X_1$, $X_2$, $X_3$, and $X_4$ being H. The preparation of this copolymer and its halogenation will be described below.

In a fifth disclosed embodiment described herein monomer I above can be copolymerized with another monomer possessing a carbon-carbon double bond to create a random copolymer, such as represented by the structure:

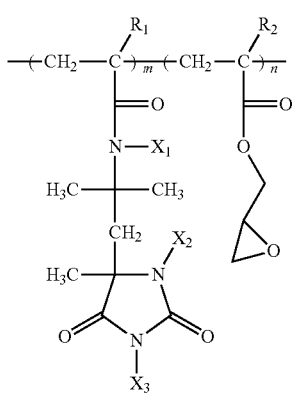

wherein $R_1$ and $R_2$ are independently H or methyl, and $X_1$, $X_2$, and $X_3$ are independently H, Cl, or Br. The ratios of coefficients m to m+n vary between 0.99 and 0.01, most preferably 0.6 to 0.4. A biocidal copolymer with the above structure has no more than two of $X_1$, $X_2$, and $X_3$ being H. The preparation of this copolymer and its halogenation will be described below.

In a sixth disclosed embodiment described herein monomer I above can be copolymerized with another monomer possessing a carbon-carbon double bond to create a random copolymer, such as represented by the structure:

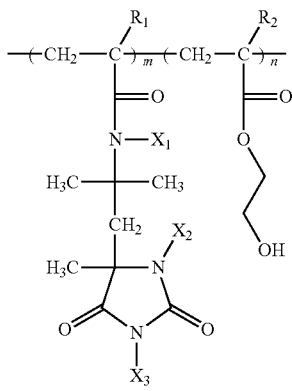

wherein $R_1$ and $R_2$ are independently H or methyl, and $X_1$, $X_2$, and $X_3$ are independently H, Cl, or Br. The ratios of coefficients m to m+n vary between 0.99 and 0.01, most preferably 0.6 to 0.4. A biocidal copolymer with the above structure has no more than two of $X_1$, $X_2$, and $X_3$ being H. The preparation of this copolymer and its halogenation will be described below.

Also described herein are compositions comprising the compounds described above. One of skill in the art can determine additional compounds or compositions that could arise from copolymerization of monomer I with other monomers possessing carbon-carbon double bonds so as to create tethering or water solubility applications. Such monomers include, but are not limited to, (3-acrylamidopropyl)trimethylammonium chloride, 2-methacryloxyethyltrimethylammonium chloride, diacetone acrylamide, methacrylamide, acrylamide, N-(hydroxymethyl)acrylamide, N-(isobutoxymethyl)acrylamide, N-hydroxyethyl acrylamide, 3-(trimethoxysilyl)propyl acrylate, 3-sulfopropyl acrylate potassium salt, butyl acrylate, ethylene glycol methyl ether acrylate, isooctyl acrylate, lauryl acrylate, methyl acrylate, octadecyl acrylate, tert-butyl acrylate, acrylic acid, sodium acrylate, methacrylic acid, sodium methacrylate, 2-(tert-butylamino)ethyl methacrylate, 2-(diethylamino)ethyl methacrylate, 2-hydroxyethyl methacrylate, 3-sulfopropyl methacrylate potassium salt, butyl methacrylate, isobutyl methacrylate, lauryl methacrylate, methyl methacrylate, [2-(methacryloyloxy)ethyl]dimethyl-(3-sulfopropyl)ammonium hydroxide, [2-(methacryloyloxy)ethyl]trimethylammonium chloride, 3-(methacryloylamino)propyl]trimethylammonium chloride, tert-butyl methacrylate, 2-allyloxyethanol, 3-allyloxy-1,2-propanediol, 3-allyloxy-2-hydroxy-1-propanesulfonic acid sodium salt, allyl acetate, vinyl alcohol, vinyl acetate, styrene, ethylene, propylene, vinyl chloride, sodium methacrylate, maleic anhydride, maleic acid, 3-(trimethoxysilyl)propyl methacrylate, 3-(triethoxysilyl)propyl acrylate, 3-(triethoxysilyl)propyl methacrylate, vinyltrimethoxysilane, triethoxyvinylsilane, and 3-allyl-1,2-epoxypropane.

These copolymers can be rendered biocidal upon halogenation with sources of oxidative chlorine or bromine.

B. Synthetic Methods

Described herein are methods for synthesizing compounds HA, HASL, HASA, HAGM, and HAOH. It is to be understood that optimization of the reaction conditions and the use of alternative reagents may be possible by those skilled in the art.

Monomer HA can be prepared by a Bucher-Berg reaction as shown below:

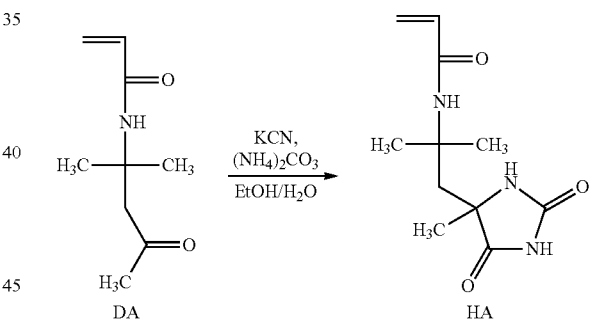

In this process 2-acrylamido-2-methyl-4-pentanone (DA) (TCI, Japan), potassium cyanide, and ammonium carbonate in a 1:2:6 molar ratio in a water/ethanol (1:1 by volume) solvent mixture can be reacted in a glass vessel at room temperature for about 4 days. After evaporation of ethanol, the crude product can be isolated by exposure to dilute HCl and filtration to produce HA as a white powder. Alternatively, the reaction could be performed in a pressure reactor at higher temperatures; e.g., about 90° C. over about 2 to 3 hours if the time variable is an issue.

A homopolymer of HA can be prepared by stirring an aqueous solution of monomer HA in the presence of initiator potassium persulfate at about 75° C. for about 5 h under nitrogen atmosphere in a glass vessel. The precipitated homopolymer can then be obtained by filtration. Nitrogen should be bubbled through the solution for about 15 min before reaction to remove any dissolved oxygen.

Copolymer HASL can be prepared by a free radical polymerization process as shown below:

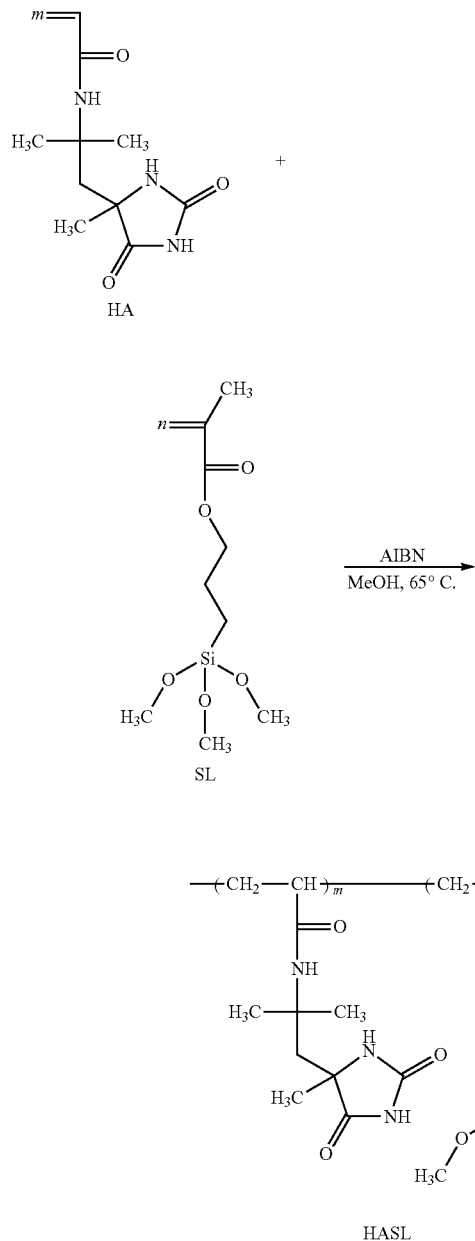

In a glass vessel monomer HA, 3-(trimethoxysilyl)propyl methacrylate (SL), initiator AIBN (2,2'-Azobis(2-methylpropionitrile)), and solvent methanol are mixed. Nitrogen should be bubbled through the solution for about 15 min to remove any dissolved oxygen. The mixture should be stirred at about 65° C. for about 2 h under nitrogen atmosphere, and then the stirring speed should be decreased due to increasing viscosity. The solvent and unreacted SL can be removed by evaporation. The resulting copolymer can be ground, dispersed in methanol, and then the solution can be filtered to remove unreacted HA. Different feed mole ratios of HA to SL (generally m to m+n are 0.99 to 0.01, preferably 0.6 to 0.4) can be used to synthesize different copolymers having varying values of m and n.

Copolymer HASA can be prepared by a free radical polymerization process as shown below:

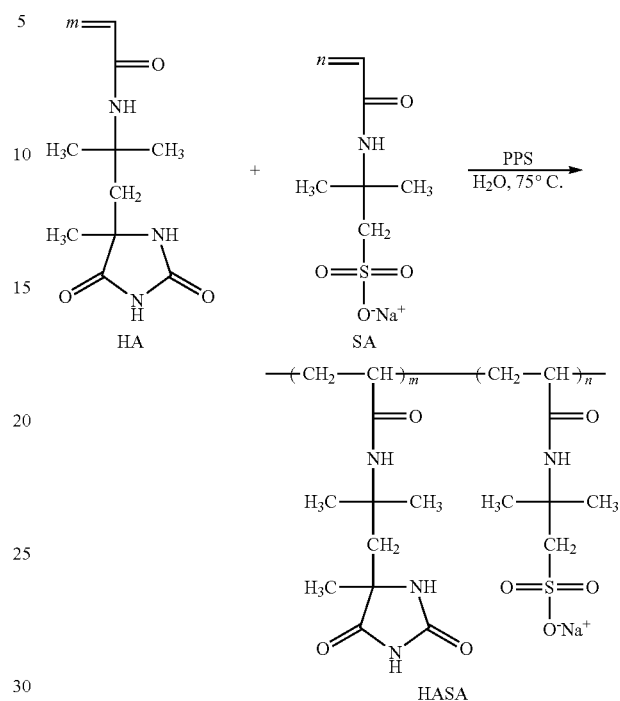

In a glass vessel monomer HA, 2-acrylamido-2-methyl-1-propanesulfonic acid, sodium salt (50 wt % solution in water) (SA), initiator potassium persulfate, and solvent water should be added. Nitrogen should be bubbled through the solution for about 15 min to remove any dissolved oxygen. The mixture should be stirred at about 75° C. for about 5 h under nitrogen atmosphere. Any precipitated homopolymer of HA and water-insoluble copolymers can be obtained by filtration, while the water-soluble copolymers can be recovered by evaporation of the water solvent. Different feed mole ratios of HA to SA (generally m to m+n are 0.99 to 0.01, preferably 0.8 to 0.7) can be used to synthesize different water-soluble or water-dispersible copolymers having varying values of m and n. Aqueous solutions of those copolymers having ratios of m to m+n of 0.7 or less will be completely homogeneous and transparent.

Copolymer HAGM can be prepared by a free radical polymerization process as shown below:

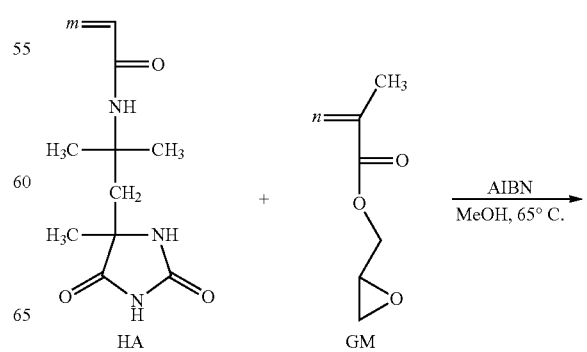

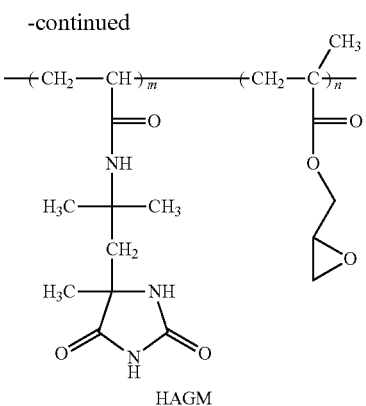

HAGM

In a glass vessel HA, glycidyl methacrylate (GM), initiator AIBN (2,2'-Azobis(2-methylpropanenitrile)), and methanol are mixed. Nitrogen should be bubbled through the solution for 15 min to remove any dissolved oxygen. The mixture should be stirred at about 65° C. for about 75 min under nitrogen protection. When the mixture is cooled to room temperature, the copolymer precipitates from the solution. The copolymer can be recovered by filtration and then further purified by rinsing with methanol. Different feed mole ratios of HA to GM (generally m to m+n are 0.99 to 0.01, preferably 0.6 to 0.4) can be used to synthesize different copolymers having varying values of m and n.

Copolymer HAOH can be prepared by a free radical polymerization process as shown below:

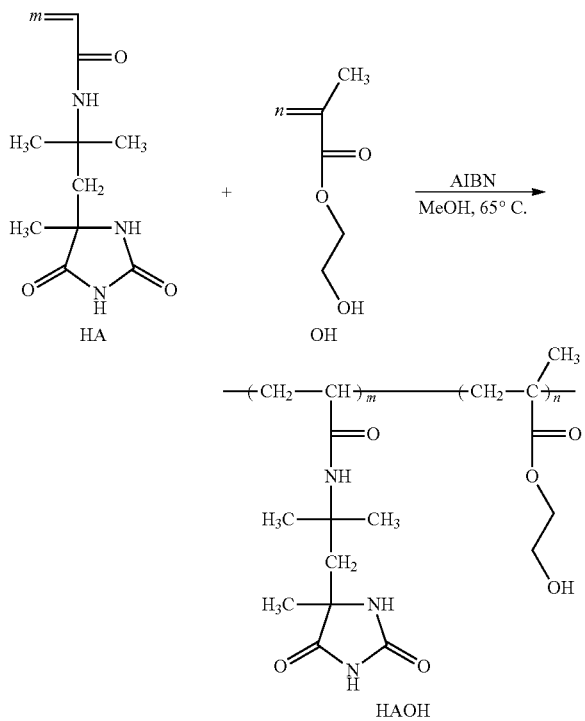

HAOH

In a glass vessel HA, 2-hydroxyethylmethacrylate (OH), initiator AIBN (2,2'-Azobis(2-methylpropanenitrile)), and methanol are mixed. Nitrogen should be bubbled through the solution for 15 min to remove any dissolved oxygen. The mixture should be stirred at about 65° C. for about 2.5 h under nitrogen protection. The solvent and unreacted OH can be removed by evaporation, and the copolymer will be obtained as white pellets. Different feed mole ratios of HA to OH (generally m to m+n are 0.99 to 0.01, preferably 0.6 to 0.4) can be used to synthesize different copolymers having varying values of m and n.

All of the compounds (monomer HA, homopolymer of HA, and the copolymers HASL, HASA, HAGM, and HAOH) can be blended into materials before or after halogenation by a mixing process. Halogenation of the compounds before or after blending can be accomplished by exposure to a source of free halogen. For chlorination the process can be conducted in aqueous solution using such sources as gaseous chlorine, sodium hypochlorite bleach, calcium hypochlorite, chloroisocyanurates, and chlorinated hydantoins. Likewise, for bromination the process can be accomplished by exposure in aqueous solution to sources, such as molecular bromine liquid, sodium bromide in the presence of an oxidizer, such as potassium peroxy monosulfate or hypochlorite bleach, and brominated hydantoins. Halogenation can also be affected in organic solvents, such as methylene chloride, employing free radical halogenating agents, such as tert-butyl hypochlorite.

For attachment to a surface of a material, in the case of the monomer or homopolymer of HA, or their halogenated derivatives, a grafting process is necessary. For example, a solution of the monomer or a dispersion of the homopolymer of HA, or their halogenated derivatives, can be exposed to the surface of the material in the presence of radiation or an initiator, such as potassium persulfate, and heat or ultraviolet photons. In the case of the copolymers or their halogenated derivatives attachment to surfaces can be affected through a grafting process, as mentioned above. However, all of the copolymers and their halogenated derivatives described herein also can be tethered to a surface by other means. In the case of HASL, upon exposure to an alcohol/water mixture, the alkoxy groups are hydrolyzed to OH groups which can then react with OH groups on cellulose, metal oxides, and the like to produce silyl ether bonds upon curing at elevated temperatures; e.g., at about 165° C. as in Example 6 below. For HASA a layer-by-layer assembly technique employing a quat monomer as the cationic species can be used. For HAGM an acetone/water solution can be used to dissolve the copolymer which can be bonded to a surface at elevated temperature (e.g., 165° C.) through opening of the epoxide ring and subsequent reaction with OH groups on cellulose, metal oxides, and the like. For HAOH it is necessary to provide crosslinking between the OH groups on the copolymer and the OH groups on cellulose, metal oxides, and the like. For this purpose 1,2,3,4-butanetetracarboxylic acid (BTCA) is a satisfactory crosslinking agent. HAOH and BTCA can be dissolved together in ethanol/water. After soaking the surface in this solution, curing can be affected at about 175° C. For all of the copolymer solutions a concentration of less than or equal to 10 wt % will provide good functional coatings. Halogenation can be accomplished before or after the coating procedures using the sources of oxidative chlorine or bromine discussed above.

C. Utility and Methods of Use

The compounds and/or compositions of the present invention can be used, for example, for producing a functionalized surface or material. An effective amount of a compound and/or composition of the present invention can be attached to or incorporated in a particular material. The method for attaching or incorporating the compound and/or composition is not critical as long as the activity of the compound and/or composition is maintained. By "effective amount" of a compound and/or composition as provided herein is meant a sufficient amount of the compound or composition to provide the desired result; i.e., biocidal efficacy. The exact amount required may depend on the material to be functionalized. Thus, it is not possible to specify an exact "effective amount". However, an appropriate effective amount can be determined by one of ordinary skill in the art by using routine experimentation.

Examples of materials that can be functionalized include, but are not limited to, cellulose, synthetic fibers, filter materials, latex paint, chitin, chitosan, glass, ceramics, plastics, rubber, cement grout, latex caulk, porcelain, acrylic films, vinyl, polyurethanes, silicon tubing, marble, metal oxides, and silica. The choice of material can be determined by one of ordinary skill in the art.

To provide biocidal activity for a material or surface, the halogenated form of the compound/composition can be, for example, attached to the surface or incorporated in the material. Alternatively, the unhalogenated compound/composition can be attached to the surface or incorporated in the material and then subsequently be halogenated. Taught herein is a method of rendering a surface or material biocidal. The method can comprise either blending or bonding a monomer, homopolymer, or copolymer of this invention with a material or to a surface, before or after oxidative halogenation. When the compound/composition is attached to a surface, it is generally effected by grafting or tethering through hydroxyl moieties. Halogenation is accomplished by exposing the blended or bonded compound/composition before or after incorporation or attachment to a source of oxidative chlorine or bromine.

The halogenated or unhalogenated precursor monomers, polymers, or copolymers can be bound to a surface or material through either covalent bonding, or adhesive interaction, depending on the nature of the surface or material. This can be accomplished by exposing the surface or material to a solution of the unhalogenated precursor monomer, polymer, or copolymer at temperatures in the range of about 0 to about 300° C., more preferably of about 20 to 180° C., for times up to about 1 h, depending on the nature of the surface or material. This can also be accomplished by exposing the surface or material to a solution of the halogenated monomer, polymer, or copolymer at temperatures in the range of about 0 to about 60° C., more preferably of about 20 to 40° C. for times up to 1 h, depending on the nature of the surface or material. The solvent for the unhalogenated monomers, polymers, and copolymers can be organic compounds such as alcohols, mixtures of organic compounds such as alcohols with water, or in the case of HASA just water. For the halogenated monomers, polymers, and copolymers alcohols should be avoided because they partially protonate the halogenated compounds liberating halogen. The solutions containing the monomers, polymers, and copolymers can be exposed to materials or surfaces by soaking, spraying, spreading, and the like. The materials or surfaces can then be cured and/or dried as described above. For latex paint containing HASA or its halogenated derivative the painted surface can be allowed to simply dry at ambient temperature.

The surface or material can be rendered biocidal if the unhalogenated precursor monomer, polymer, or copolymer is exposed to a solution of oxidative halogen before or after blending or binding with or to a material or surface. Examples of sources of oxidative chlorine include. but are not limited to, gaseous chlorine, sodium hypochlorite bleach, calcium hypochlorite, chloroisocyanurates, and chlorinated hydantoins in aqueous solution or tert-butyl hypochlorite in an organic solvent such as methylene chloride. Examples of oxidative bromine include, but are not limited to, molecular bromine liquid, sodium bromide in the presence of an oxidizer, such as potassium peroxy monosulfate or hypochlorite bleach, and brominated hydantoins. For example, an aqueous solution of 5% to 10% household bleach can be used for efficient chlorination, which can be accomplished at ambient temperature by spraying, soaking, or wiping the material or surface with the same. After halogenation, the surface or material should be allowed to dry in air at temperatures up to 40° C., although ambient temperatures are preferable if time permits, and then it should be rinsed with water. The surface or material will then exhibit biocidal properties for various time periods dependent upon the composition of the surface or material, the use pattern (contact with microorganisms or virus particles and halogen demand), the storage temperature, etc. When the bound halogen content becomes too low for efficient biocidal activity, the surface or material can be recharged with halogen in the same manner as for the original charging noted above.

One of skill in the art can determine alternative methods of attaching, incorporating, or otherwise adding a compound/composition of the present invention to a material or surface, and the methods described here are not meant to be limiting.

There are several marked advantages of the biocidal materials and surfaces of this invention over prior technology. For example, the present compounds/compositions are much more effective biocidally against pathogenic microorganisms, such as *Staphylococcus aureus* and *Escherichia coli* and virus particles, than are commercially available biocides, such as quaternary ammonium salts, requiring only a few minutes to achieve complete inactivation, as opposed to hours, for the quats. Thus, the present compounds/compositions are advantageous for numerous medical applications in hospitals, nursing homes, research laboratories, and the home/work place. The compounds/compositions are also effective at inactivation of odor- and color-causing non-pathogenic organisms, such as mildew. The compounds/compositions of this invention are also considerably more resistant to degradation and loss of halogen in the presence of ultraviolet light than are prior reported N-halamine materials. This allows extended exposure to sunlight for halogenated coatings on military and emergency responder clothing. A few examples of surfaces and materials which can be made biocidal with the present invention include, but are not limited to, surgical gowns and gloves, sheets, bandages, sponges, tables, counter tops, plastics, tent liners, synthetic fibers, wood items, grout, caulk, porcelain, polyurethanes, and shower stalls.

The present invention is more particularly described in the following examples, which are intended as illustrative only since numerous modifications and variations therein will be apparent to those skilled in the art.

EXAMPLES

Example 1

Preparation of Compound HA

Most chemicals were purchased from Sigma-Aldrich (Saint Louis, Mo.) and used without further purification unless otherwise stated. 2-acrylamido-2-methyl-1-(5-methylhydantoinyl)propane (HA) was prepared by the reaction of 2-acrylamido-2-methyl-4-pentanone (TCI, Japan), potassium cyanide, and ammonium carbonate in a 1:2:6 molar ratio in a water/ethanol (1:1 by volume) solvent mixture in a round flask at room temperature for 4 d. After evaporation of ethanol, the crude product was isolated by exposure to dilute HCl and filtration. The product was obtained as a white powder having a melting point of 178° C. and a yield of 89%. Its structure was confirmed by NMR (Bruker 400 MHz spectrometer; $^1$H and $^{13}$C spectra were recorded with 16 and 1024 scans, respectively), FTIR (Nicolet 6700 FTIR spectrometer with an ATR (Attenuated Total Reflectance) accessory, recorded with 32 scans at 2 cm$^{-1}$ resolution), and mass spectroscopy (LCMS (Waters® Acquity HPLC™ and Q-T of Premier™). $^1$H NMR (DMSO-d$_6$, 400 MHz) δ 1.23 (3H), 1.25 (3H), 1.29 (3H), 2.15 (2H), 5.49 (1H), 6.01 (1H), 6.22 (1H), 7.58 (1H), 7.81 (1H), 10.58 (1H). $^{13}$C NMR (DMSO-d$_6$, 100 MHz) δ 178.65, 163.82, 155.99, 132.77, 124.07, 61.03, 52.35, 43.94, 27.53, 27.08, 26.33. FTIR (ATR, cm$^{-1}$) 3353, 3203, 3076, 1759, 1720, 1704, 1665, 1649, 1564, 1532, 1252, 979, 735, 634, 608. LC/MS (M+H)$^+$: 240.1358. The molecular weight of HA was measured by mass spectrometry to be 239.128, while the calculated mass for HA is 239.127 g/mol.

Example 2

Preparation of Copolymer HASL

The hydantoin acrylamide siloxane copolymers (HASL) were prepared by free radical polymerization. As a general example, in a 50 mL round-bottom flask, 1.44 g (6 mmol) of HA, 1.54 g (6 mmol) of 3-(trimethoxysilyl)propyl methacrylate (SL), 0.03 g of AIBN (2,2'-Azobis(2-methylpropanenitrile)), and 5 mL MeOH were added. Nitrogen was bubbled through the solution for 15 min to remove any dissolved oxygen. The mixture was stirred at 65° C. for 2 h, and then the stirring speed was decreased due to increasing viscosity. The solvent and unreacted SL were removed by evaporation. The resulting copolymer was ground, dispersed in MeOH, and then filtered to remove unreacted HA. Different mole ratios of HA to SL (0.2 to 5) were used to synthesize five different copolymers as summarized in Table 1. The oxidative chlorine loadings for each copolymer are also shown in Table 1.

TABLE 1

Composition of the Synthesized Copolymers.

| Copolymer | $M_{HA}$/ $M_{HA}$ + $M_{SL}$ | $m_{HA}$/ $m_{HA}$ + $m_{SL}$ | Wt % copolymer on cotton[b] | Theoretical Cl$^+$ % on cotton[c] | Measured Cl$^+$ % on cotton |
|---|---|---|---|---|---|
| 15 | 0.17 | 0.14 | 2.95 | 0.12 | 0.09 |
| 13 | 0.25 | 0.22 | 2.92 | 0.18 | 0.13 |
| 11 | 0.50 | 0.41 | 2.81 | 0.30 | 0.26 |
| 31 | 0.75 | 0.70 | 2.40 | 0.39 | 0.30 |
| 51 | 0.83 | 0.78 | 2.37 | 0.40 | 0.32 |

[a]$M_{HA}$ and $M_{SL}$: mole fraction of HA and SL in feed, $m_{HA}$ and $m_{SL}$: mole fraction of HA and SL in copolymer according to $^1$H NMR analysis.
[b]Calculated according to weight gain of the cotton fabric before and after the coating.
[c]Calculated assuming around 60% of the total N—H moieties were chlorinated.

Example 3

Preparation of Copolymers HASA

The HA homopolymer and copolymers with 2-acrylamido-2-methyl-1-propanesulfonic acid, sodium salt (SA) were synthesized by free radical polymerization. For example, to prepare copolymer 9 (Table 2), in a 100 mL round bottom flask, 2.15 g (9 mmol) of HA, 0.46 g (1 mmol) 2-acrylamido-2-methyl-1-propanesulfonic acid, sodium salt (50 wt % solution in water), 0.01 g potassium persulfate, and 50 mL of distilled water were added. Nitrogen was bubbled through the solution for 30 min before reaction to remove any dissolved oxygen. The mixture was stirred at 75° C. for 5 h under nitrogen atmosphere. The precipitated homopolymer was obtained by filtration, while the copolymers were recovered by evaporation of the water solvent. The yields were about 90 wt % in all cases. Different feed mole ratios of SA to HA were used to synthesize four different copolymers as summarized in Table 2. Copolymers containing SA at higher ratios than 30% (6, 5, etc.) were not prepared since 7 was adequately soluble in water, and copolymers containing increased ratios of HA would load higher amounts of oxidative chlorine. The intrinsic viscosities of polymers 10, 9, 8, and 7 were 0.88, 0.92, 1.10, and 1.15 dL/g (in dimethylsulfoxide, 25° C.), respectively.

TABLE 2

Composition of the Synthesized Polymers as Expected from the Feed Ratios of HA and SA.

| Polymer | $M_{HA}$/ ($M_{HA}$ + $M_{SA}$)[a] | Appearance in water |
|---|---|---|
| 10 | 1.0 | Insoluble |
| 9 | 0.9 | Colloid (opaque) |
| 8 | 0.8 | Colloid (translucent) |
| 7 | 0.7 | Soluble (transparent) |

[a]$M_{HA}$ and $M_{SA}$: mole fraction of HA and SA in the feed mixture.

NMR and FTIR analyses were used to confirm the structures of the synthesized polymers. The primary evidence for the polymer formation was the disappearance of the vinyl proton signals between 5.5 and 6.5 ppm. For the homopolymer 10, the signal at 1.26 ppm can be assigned to the protons of the methyl groups. The signals at 7.87 ppm and 10.59 ppm can be assigned to the amide and imide protons of the hydantoin ring, respectively. In the spectrum for 9, a new signal appeared at around 1.37 ppm as compared to the spectrum for 10, due to methyl groups of the comonomer SA. The intensity of this band enhances by increasing the amount of SA in the copolymer (9 to 7). Unfortunately the resolution in the spectra, even for dilute samples, was not sufficient for an accurate determination of the mole ratios of units HA and SA in the copolymers. However, the mole feed ratios should give a reasonable account of the copolymer compositions since the acryl amide monomer units in HA and SA are the same in structure.

The FTIR spectra of the polymers were also suggestive of the copolymer formation and the monomer composition. First, the stretching vibration for the vinyl bonds of the monomers at around 1630 cm$^{-1}$ disappeared for the polymers. Also, the bands in the spectra were broader as compared to those of the comonomers due to polymerization. The bands at 1709 and 1760 cm$^{-1}$ are characteristic of the presence of the hydantoin ring in the polymers; the intensities of these bands decreased concomitant with the reduction in amount of HA in the copolymers. The intensities of the SO$^-$ group asymmetric stretching band at around 1180 cm$^{-1}$ and the symmetric stretching band at 1039 cm$^{-1}$ (25) increased with increasing SA amount in the copolymers.

Example 4

Preparation of Copolymers HAGM

The hydantoin acrylamide glycidyl methacrylate copolymers (HAGM) were prepared by free radical polymerization. As a general example, in a 50 mL round-bottom flask, 1.91 g (8 mmol) of HA, 1.17 g (8 mmol) of glycidyl methacrylate (GM)(Alfa Aesar, Heysham, UK), 0.031 g of AIBN (2,2'-

Azobis(2-methylpropanenitrile)), and 10 mL of methanol were mixed. Nitrogen was bubbled through the solution for 15 min to remove any dissolved oxygen. The mixture was stirred at 65° C. for 75 min under nitrogen protection. When the mixture was cooled to room temperature, the copolymer precipitated from the solution. The copolymer was recovered by filtration and then further purified by rinsing with methanol.

Example 5

Preparation of Copolymers HAOH

The hydantoin acrylamide 2-hydroxyl methacrylate copolymers (HAOH) were prepared by free radical polymerization. As a general example, in a 50 mL round-bottom flask, 1.44 g (6 mmol) of HA, 0.82 g (6 mmol) of 2-hydroxyethylmethacrylate (OH)(TCI, Tokyo, JP), 0.023 g of AIBN (2,2'-Azobis(2-methylpropanenitrile)), and 5 mL of methanol were mixed. Nitrogen was bubbled through the solution for 15 min to remove any dissolved oxygen. The mixture was stirred at 65° C. for 2.5 h under nitrogen protection. The solvent and unreacted OH were removed by evaporation, and the copolymer was obtained as white pellets.

Example 6

Coating with HASL Copolymers and Subsequent Chlorination

Copolymer HASL was coated onto cotton fibers as follows. The synthesized copolymers were first dissolved in an ethanol/water mixture (3:2 by weight) at a concentration of 3 wt %. The mixture was stirred for 15 min to produce a uniform solution. Cotton swatches (Style 400 Bleached 100% Cotton Print Cloth from Testfabrics, Inc., West Pittston, Pa.) in the size of 320 $cm^2$ were soaked in the coating solution (50 g) for 15 min, then uniformly padded through a laboratory wringer (Birch Brothers Southern, Waxhaw, N.C.), and then cured at 165° C. for 1 h. After curing, the swatches were soaked in a 0.5% detergent solution for 15 min, rinsed several times with water, and were conditioned in a standard environment, (21° C., 65% RH).

The treated fabrics were chlorinated by soaking in a 1% aqueous solution of household bleach (6% sodium hypochlorite) at pH 7 (adjusted with 6 N HCl) for 30 min. After rinsing with tap and distilled water, the swatches were then dried at 45° C. for 1 h to remove any unbonded chlorine from the material. The chlorine concentrations loaded onto the coated samples compounds were determined by an iodometric/thiosulfate titration procedure. The weight percent $Cl^+$ on the samples was calculated by the following formula;

$$Cl^+(\%)=(N \times V \times 35.45)/(2 \times W) \times 100 \quad (1)$$

where $Cl^+(\%)$ is the weight percent of oxidative chlorine on the samples, N and V are the normality (equiv/L) and volume (L) of the titrant sodium thiosulfate, respectively, and W is the weight of the sample in g.

Example 7

Coating with HASA Copolymers in Latex Paint and Subsequent Chlorination

For example, to prepare a 1.5 wt % polymer in paint (a commercial interior white latex paint (Olympic®, PPG Architectural Finishes, Inc., Pittsburgh Pa.) including a total solid content of 48 wt % (titanium dioxide, vinyl acetate/ethylene copolymer, sodium potassium aluminum silicate, calcium carbonate, aluminum silicate) was used in this study), the synthesized polymers (0.36 g) were first dispersed/dissolved in distilled water (5.64 g) by stirring for 1 h to produce a uniform solution. In a vial 1.1 g of the polymer dispersion/solution and around 9.1 g of the paint were added and stirred for 30 min to produce a uniform mixture. Then the mixture was poured onto a polyester transparency slide of size of 21.5×27.9 cm. The slide provided a non-porous surface that was easily coated uniformly with the paint. The slide itself did not absorb bleach or change shape during the chlorination and heating procedures and provided uniform contact with the bacterial suspensions. The paint was uniformly spread onto the transparency slide with a foam roller. The painted transparencies were dried for 1 week at room temperature. The amounts of the paint on the transparencies were about 15 wt % of the total weight.

The painted transparencies were generally chlorinated by soaking in a 10% aqueous solution of household bleach (6% sodium hypochlorite) at pH 7 (adjusted with 6 N HCl) for 1 h. For comparison purposes, a sample of copolymer 9 on a transparency was also chlorinated by wiping the surface with the dilute bleach for about 5 s. After rinsing with tap and distilled water, the transparencies were then dried at 45° C. for 1 h to remove any unbonded chlorine from the material. The chlorine concentrations loaded onto the coated samples were determined by a modified iodometric/thiosulfate titration procedure in which the samples (2.5×7.6 cm) were placed in a solution containing 90 mL of ethanol and 10 mL of 0.01N acetic acid. After the addition of 0.2 g of potassium iodide, 0.00375 N sodium thiosulfate was used to titrate until the disappearance of the yellow color at the end point. The weight percent $Cl^+$ on the samples was calculated by the following formula;

$$Cl^+(\%)=[(N \times V \times 35.45)/(2 \times W)] \times 100 \quad (2)$$

where $Cl^+(\%)$ is the weight percent of oxidative chlorine on the samples, N and V are the normality (equiv/L) and volume (L) of the titrant sodium thiosulfate, respectively, and W is the weight of the sample in g.

The amount of the chlorine loadings, both weight percent with respect to the paint and chlorine atoms per $cm^2$ on the treated paints are summarized in Table 3. The paint containing no polymer could be chlorinated at a very low chlorine loading of about 0.04 wt %. The chlorine loadings of the treated paints with 1 wt % polymer were between 0.21 and 0.32 wt %. The chlorine loadings of the treated paints with 1.5 wt % polymer were higher as compared to those containing 1 wt % polymer as expected. The measured chlorine loadings of the treated paints were near the theoretical chlorine loadings indicating that most of the N—H moieties in the paint matrix could be chlorinated. A sample treated with copolymer 9 and wiped with the dilute bleach for about 5 s, then dried, rinsed, and further dried at 45° C. for 1 h provided a 0.25 wt % chlorine loading. The immersion technique described above used on an identical sample containing copolymer 9 provided a 0.38 wt % loading, which was higher than that for the wiping technique as expected. However, the loading provided by the wiping procedure would be easily adequate for a biocidal application.

TABLE 3

Chlorine Loadings of the Biocidal Paints.

| | 1 wt % copolymer in paint | | 1.5 wt % copolymer in paint | |
|---|---|---|---|---|
| Sample | [Cl$^+$] %$^a$ | [Cl$^+$] atoms/cm$^2$ | [Cl$^+$] %$^a$ | [Cl$^+$] atoms/cm$^2$ |
| 10 | 0.31 | 1.7 × 10$^{17}$ | 0.47 | 2.2 × 10$^{17}$ |
| 9 | 0.27 | 1.3 × 10$^{17}$ | 0.40 | 1.7 × 10$^{17}$ |
| 8 | 0.24 | 9.6 × 10$^{16}$ | 0.39 | 1.7 × 10$^{17}$ |
| 7 | 0.21 | 7.4 × 10$^{16}$ | 0.32 | 1.2 × 10$^{17}$ |
| Paint$^b$ | 0.04 | 1.7 × 10$^{16}$ | 0.04 | 1.7 × 10$^{16}$ |

$^a$[Cl$^+$] is the chlorine loading on the treated paint samples in weight percent with respect to the paint weights (before exposure to light).
$^b$Paint with no polymer added (before exposure to light).

The paint matrix allowed halogenation of the N-halamine polymers not only on the surface, but also within the paint. Moreover, even the water-soluble copolymer 7 was well trapped in the paint matrix as well as on the surface as evidenced by FTIR; i.e., an additional band appeared at 1648 cm$^{-1}$ when copolymer 7 was added into the paint, and this band remained after aqueous chlorination indicating that the copolymer was well trapped in the paint matrix. Similar FTIR spectra were also observed with the other polymers.

Example 8

Coating with HAGM Copolymers and Subsequent Chlorination

Copolymer HAGM was coated onto cotton fibers as follows. The synthesized copolymer was first dissolved in an acetone/water mixture (3:2 by weight) at a concentration of 4 wt %. The mixture was stirred for 15 min to produce a uniform solution. Cotton swatches (Style 400 Bleached 100% Cotton Print Cloth from Testfabrics, Inc., West Pittston, Pa.) were soaked in the coating solution for 15 min, then uniformly padded through a laboratory wringer (Birch Brothers Southern, Waxhaw, N.C.), and then cured at 165° C. for 1 h. After curing, the swatches were soaked in a 0.5% detergent solution for 15 min, rinsed several times with water, and were conditioned in a standard environment, (21° C., 65% RH).

The treated fabrics were chlorinated by soaking in a 10% aqueous solution of household bleach (6% sodium hypochlorite) at pH 7 (adjusted with 6 N HCl) for 1 h. After rinsing with tap and distilled water, the swatches were then dried at 45° C. for 1 h to remove any unbonded chlorine from the material. The chlorine concentrations loaded onto the coated samples were determined by an iodometric/thiosulfate titration procedure. The weight percent Cl$^+$ on the samples was calculated by the following formula;

$$Cl^+(\%) = (N \times V \times 35.45)/(2 \times W) \times 100 \quad (3)$$

where Cl$^+$(%) is the weight percent of oxidative chlorine on the samples, N and V are the normality (equiv/L) and volume (L) of the titrant sodium thiosulfate, respectively, and W is the weight of the sample in g.

Example 9

Coating with HAOH Copolymers and Subsequent Chlorination

Copolymer HAOH was coated onto cotton fibers using 1,2,3,4-butanetetracarboxylic acid (BTCA) as a crosslinking agent. The synthesized copolymer was first dissolved in an ethanol/water mixture (3:2 by weight) at a concentration of 3 wt %. To that solution, 5.7 wt % BTCA was added, and the mixture was stirred until BTCA was completely dissolved. Cotton swatches (Style 400 Bleached 100% Cotton Print Cloth from Testfabrics, Inc., West Pittston, Pa.) were soaked in the coating solution for 15 min, then uniformly padded through a laboratory wringer (Birch Brothers Southern, Waxhaw, N.C.). The immersed swatches were dried at 130° C. for 10 min, followed by curing at 175° C. for 5 min. Finally, the swatches were soaked in a 0.5% detergent solution for 15 min, rinsed several times with water, and were conditioned in a standard environment, (21° C., 65% RH).

The treated fabrics were chlorinated by soaking in a 10% aqueous solution of household bleach (6% sodium hypochlorite) at pH 7 (adjusted with 6 N HCl) for 1 h. After rinsing with tap and distilled water, the swatches were then dried at 45° C. for 1 h to remove any unbonded chlorine from the material. The chlorine concentrations loaded onto the coated samples were determined by a iodometric/thiosulfate titration procedure. The weight percent Cl$^+$ on the samples was calculated by the following formula;

$$Cl^+(\%) = (N \times V \times 35.45)/(2 \times W) \times 100 \quad (4)$$

where Cl$^+$(%) is the weight percent of oxidative chlorine on the samples, N and V are the normality (equiv/L) and volume (L) of the titrant sodium thiosulfate, respectively, and W is the weight of the sample in g.

Example 10

Stability Testing for the HASL Copolymers and their Chlorinated Derivatives The stability and rechargeability of chlorine on the cotton samples were evaluated by using a standard washing test according to AATCC Test Method 61. The cotton samples were washed for the equivalents of 5, 10, 25, and 50 machine washes in a Launder-Ometer. The Cl$^+$% loadings on the samples after the washings were determined by the titration procedure mentioned above.

UVA light stability of the bound chlorine and the coatings on cotton fabric samples were determined using an Accelerated Weathering Tester (The Q-panel Company, Cleveland, Ohio, USA). The samples were placed in the UV (Type A, 315-400 nm) chamber for contact times ranging up to 24 h. After specific times of exposure to UVA irradiation, the samples were removed from the UV chamber and titrated, or rechlorinated and titrated. The temperature was 37.6° C., and the relative humidity was 17% during the UVA light irradiation. The UV chamber provided an irradiance of 0.68 W/m$^2$ at 340 nm, which approximates the irradiance provided by noon summer sunlight.

The stabilities toward machine washing of coated fabric swatches are presented in Table 4. Three types of washing experiments were performed: prechlorinated coatings at the concentration levels indicated at 0 machine washes Table 4 (C), prechlorinated and rechlorinated after a given number of machine washes (R), and unchlorinated until after a given number of machine washes (U). Several observations can be made pertaining to the data in Table 3. First, the initial chlorine loading of the coated fabrics (0 machine washes) increased by increasing the amount of HA in the copolymer composition 15 to 51 due to increased N—H sites in the copolymers. For 15, 13, and 11, the prechlorinated coatings (C) lost most of their initial chlorine loadings within 10 to 25 washes. However, this rate refers to the N—Cl bond dissociation, and is not a result of the dissociation of tethering groups (siloxane) from cotton because rechlorination of the copolymers provided chlorine loadings (R) at about their initial values. All of the unchlorinated copolymers (U) are also very resistant toward decomposition during washing cycles. On the other hand, for 31 and 51, the prechlorinated coatings (C) again lost most of their initial chlorine loadings within 10 to 25 washes, and this rate is related to both N—Cl bond breakage and the dissociation of tethering siloxane groups from cotton because of the decreasing chlorine loadings after rechlorination (R). The unchlorinated copolymers 31 and 51 (U) were also not very resistant (compared to 15,13, and 11) toward washing cycles.

TABLE 4

Stability toward Washing of Cotton Coated with Synthesized Copolymers (Cl$^+$ % Remaining).

| MW[a] | 15 | | | 13 | | | 11 | | |
|---|---|---|---|---|---|---|---|---|---|
| | C | R | U | C | R | U | C | R | U |
| 0 | 0.09 | 0.09 | | 0.13 | 0.13 | | 0.26 | 0.26 | |
| 5 | 0.02 | 0.08 | 0.09 | 0.02 | 0.13 | 0.11 | 0.08 | 0.26 | 0.22 |
| 10 | 0.01 | 0.08 | 0.09 | 0 | 0.12 | 0.11 | 0.06 | 0.26 | 0.23 |
| 25 | 0 | 0.08 | 0.09 | 0 | 0.12 | 0.11 | 0.03 | 0.24 | 0.23 |
| 50 | 0 | 0.07 | 0.08 | 0 | 0.11 | 0.10 | 0 | 0.23 | 0.23 |

| | 31 | | | 51 | | |
|---|---|---|---|---|---|---|
| | C | R | U | C | R | U |
| 0 | 0.30 | 0.30 | | 0.32 | 0.32 | |
| 5 | 0.09 | 0.28 | 0.30 | 0.02 | 0.07 | 0.28 |
| 10 | 0.05 | 0.21 | 0.30 | 0.01 | 0.03 | 0.27 |
| 25 | 0.03 | 0.17 | 0.26 | 0 | 0.02 | 0.23 |
| 50 | 0 | 0.12 | 0.24 | 0 | 0.02 | 0.23 |

[a]MW: Machine washes,
[b]C: Chlorinated before washing, R: Chlorinated before washing and rechlorinated after washing, U: Unchlorinated before washing, but chlorinated after washing,
[a]The error in the measured Cl$^+$ weight percentage values was ±0.01.

The stability of the copolymers on cotton increased by increasing the amount of the siloxane group (SL) in the copolymer composition. Since copolymer 11 gave the highest chlorine loading between the most wash stable copolymers (15, 13, and 11), further experiments were conducted with copolymer 11. The stability of the copolymers 15, 13, and 11 on cotton was also quite high compared to previous studies done with similar N-halamine monomeric siloxane coatings (see Kocer, H. B., et al., "Effect of Alkyl Derivatization on Several Properties of N-halamine Biocidal Siloxane Coatings", Ind. Eng. Chem. Res. 2008, 47, 7558; Liang, J., et al., "Improved Biocidal Siloxane", Ind. Eng. Chem. Res. 2007, 46, 1861.) This might be explained by hydrolysis of the siloxane tethering groups resulting in removal of the prior N-halamine moieties from the surface. However, for the polymeric coatings described herein, a number of siloxane groups tether the long chain polymers onto surface, and hydrolysis of a portion of the siloxane groups does not result in removal of the whole polymer chain from the surface.

FIG. 1 illustrates the stabilities of copolymer 11 and the chlorinated copolymer 11 (11-Cl) on cotton toward UVA degradation following a series of rechlorinations; the data for 11 represent chlorination after UVA exposure of the unchlorinated samples at the indicated UVA contact times. The losses of chlorine between points shown in FIG. 1 after 24 h of exposure would not be expected to be linear as shown in the graph; intermediate points were not taken. 11-Cl lost only 50% of the bound chlorine slowly within 24 h, and the remaining chlorine loading (0.12%) would be capable of providing a biocidal function. The UVA exposed 11-Cl was almost completely rechlorinated after 24 h (R$_1$); however, following UVA exposure cycles, and rechlorinations (R$_2$-R$_8$), a progressive decline in chlorine loading occurred. This decline might be due to an intermolecular rearrangement of the chlorine atom onto the carbon atoms adjacent to the Si atom resulting in Si-carbon bond cleavage as observed previously for another n-halamine siloxane (Kocer, H. B., et al., "Mechanism of Photolytic Decomposition of N-halamine Biocidal Siloxane Coatings", ACS Appl. Mater. Interfaces, 2010, 2, 2456). On the other hand, unchlorinated 11 on cotton exhibited no significant decomposition in the presence of the UVA irradiation over the entire 192 h of exposure. The stabilities were quite remarkable given that a six hour exposure in the UV chamber was equivalent to the same time in direct midday summer sunlight.

Example 11

Stability Testing for the Chlorinated HASA Copolymers

Under ambient lighting in air, the paint samples slowly lose their chlorine contents. For example, a dried sample of copolymer 9 at the 1.5 wt % concentration level in the latex paint loaded initially with 0.38 wt % chlorine declined in chlorine loading to 0.16 wt % over an 8 wk period. However, at that time it was rechlorinated with dilute household bleach to a chlorine level of 0.39 wt % indicating that there was no decomposition of the copolymer in the paint. In an application, surfaces coated with the treated paints could be periodically rechlorinated to maintain biocidal efficacy. Since the copolymers are water soluble, their retention in the dried paint was assessed. Sample transparencies treated with copolymer 7 and copolymer 9 were exposed to flowing tap water (750 mL/min) for 24 h. The chlorine content for copolymer 7 declined from 0.31 to 0.23 wt % over the time period, but it could be rechlorinated to 0.29 wt %. For copolymer 9 the decline was from 0.38 to 0.29 wt % with rechlorination to 0.37 wt %. Thus, loss of the copolymers from the dried paint samples upon exposure to flowing water was minimal.

The stabilities toward UVA light of the polymer-added paints as determined as described in Example 10 are presented in Table 5. The initial chlorine loadings of the treated paints were between 0.30 and 0.46 wt %. The loss of the bound chlorine from the treated paints was rapid within the first two days of UVA light exposure, but then became slower. Previous studies in these laboratories have shown that the bound chlorine on N-halamines is vulnerable to UVA light exposure with a total bound chlorine loss generally within hours to a few days. However, the chlorinated polymers in the paint matrix showed excellent stability toward UVA light exposure; this is probably due to the protection of the chlorinated polymers from the UVA photons provided by the paint matrix. The loss of the bound chlorine in the copolymers 9-Cl, 8-Cl, and 7-Cl were 46%, 59%, and 60%, respectively, while the loss in homopolymer 10-Cl was only 40%. The bound chlorine losses in the copolymers were higher compared to the loss in the homopolymer, probably due to the protection of the inner layers of the insoluble homopolymer particles from the light photons. The UVA light exposed samples were rechlorinated and then further exposed to UVA light three times. All of the polymers showed excellent recharge characteristics throughout the repeated UVA light exposure and rechlorination cycles.

TABLE 5

Stability of the Treated Paints toward UVA Photons ($Cl^+$ wt % Remaining).

| Time (days)   | 10-Cl | 9-Cl | 8-Cl | 7-Cl |
|---------------|-------|------|------|------|
| 0             | 0.46  | 0.37 | 0.34 | 0.30 |
| 1             | 0.42  | 0.26 | 0.27 | 0.21 |
| 2             | 0.41  | 0.26 | 0.22 | 0.19 |
| 3             | 0.35  | 0.25 | 0.21 | 0.18 |
| 4             | 0.35  | 0.25 | 0.20 | 0.18 |
| 5             | 0.32  | 0.23 | 0.18 | 0.13 |
| 6             | 0.31  | 0.22 | 0.17 | 0.13 |
| 7             | 0.30  | 0.21 | 0.16 | 0.13 |
| 14            | 0.28  | 0.20 | 0.14 | 0.12 |
| Rechlorination| 0.45  | 0.37 | 0.33 | 0.28 |
| 28            | 0.30  | 0.22 | 0.18 | 0.16 |
| Rechlorination| 0.44  | 0.38 | 0.34 | 0.30 |
| 42            | 0.31  | 0.22 | 0.17 | 0.16 |
| Rechlorination| 0.42  | 0.35 | 0.30 | 0.27 |
| 70            | 0.23  | 0.17 | 0.15 | 0.11 |
| Rechlorination| 0.44  | 0.34 | 0.32 | 0.26 |

Example 12

Stability Testing for the HAGM Copolymers and their Chlorinated Derivatives

The stability and rechargeability of chlorine on the cotton samples were evaluated by using a standard washing test according to AATCC Test Method 61. The cotton samples were washed for the equivalents of 5, 10, 25, and 50 machine washes in a Launder-Ometer. The $Cl^+$% loadings on the samples after the washings were determined by the titration procedure mentioned above.

UVA light stability of the bound chlorine and the coatings on cotton fabric samples were determined using an Accelerated Weathering Tester (The Q-panel Company, Cleveland, Ohio, USA). The samples were placed in the UV (Type A, 315-400 nm) chamber for contact times ranging up to 24 h. After specific times of exposure to UVA irradiation, the samples were removed from the UV chamber and titrated, or rechlorinated and titrated. The temperature was 37.6° C., and the relative humidity was 17% during the UVA light irradiation. The UV chamber provided an irradiance of 0.68 W/m² at 340 nm which approximates the irradiance provided by noon summer sunlight.

The stabilities toward machine washing of coated fabric swatches are presented in Table 6. In general, the coatings exhibited remarkable washing stabilities and durabilities. After the equivalent of 50 times of laundering, around 30% of the oxidative chlorine remained on the surface (C column). Moreover, upon rechlorination at the end of 50 machine washings (R column), 80% of the initial chlorine could be restored revealing that the loss in C column was due mostly to N—Cl bond dissociation rather than the coating being washed away from cotton surface. Unlike for previously studied N-halamine coatings, there was almost no difference between the data in the R and U columns.

TABLE 6

Stability toward Washing of Cotton Coated with Synthesized HAGM Copolymer ($Cl^+$ % Remaining).

| $MW^a$ | $C^b$ | $R^b$ | $U^b$ |
|--------|-------|-------|-------|
| 0      | 0.36  |       |       |
| 5      | 0.18  | 0.34  | 0.33  |
| 10     | 0.14  | 0.32  | 0.32  |
| 25     | 0.11  | 0.31  | 0.30  |
| 50     | 0.10  | 0.29  | 0.29  |

[a]MW: Machine washes,
[b]C: Chlorinated before washing, R: Chlorinated before washing and rechlorinated after washing, U: Unchlorinated before washing, but chlorinated after washing, The error in the measured $Cl^+$ weight percentage values was ±0.01.

UVA light stabilities of the coatings are illustrated in Table 7. UVA light caused a progressive decline in chlorine loadings of the fabric. Even though 65% of the initial chlorine was lost from the surface upon one day of UVA exposure, the remaining chlorine (0.11%) would still provide an effective biocidal activity. Rechlorinations performed at one day exposure intervals revealed that there is a slight photodecomposition taking place for the chlorinated swatches. However, the magnitude of this decomposition was not as severe as observed in some of the previously studied N-halamine coatings (see Ren, et al., "Antimicrobial Efficacy and Light Stability of N-halamine Siloxanes bound to Cotton", Cellulose. 2008, 15, 593).

TABLE 7

Stability toward UVA Light of Cotton Coated with Synthesized HAGM Copolymer $Cl^+$ %$^a$ Remaining).

| Time (h) | Chlorinated | Unchlorinated |
|----------|-------------|---------------|
| 0        | 0.32        |               |
| 1        | 0.24        |               |
| 2        | 0.21        |               |
| 3        | 0.19        |               |
| 6        | 0.16        |               |
| 12       | 0.14        |               |
| 24       | 0.11        |               |
| $24R_1^a$| 0.28        | 0.31          |
| 48       | 0.08        |               |
| $48R_2$  | 0.25        | 0.33          |
| 72       | 0.09        |               |
| $72R_3$  | 0.24        | 0.31          |

[a]$R_1$ to $R_3$ indicate rechlorination of samples after UVA exposure for the specified time intervals. The error in the measured $Cl^+$ weight percentage values was ±0.01.

Example 13

Stability Testing for the HAOH Copolymers and their Chlorinated Derivatives

The stability and rechargeability of chlorine on the cotton samples were evaluated by using a standard washing test according to AATCC Test Method 61. The cotton samples were washed for the equivalents of 5, 10, 25, and 50 machine washes in a Launder-Ometer. The $Cl^+$% loadings on the samples after the washings were determined by the titration procedure mentioned above.

UVA light stability of the bound chlorine and the coatings on cotton fabric samples were determined using an Accelerated Weathering Tester (The Q-panel Company, Cleveland, Ohio, USA). The samples were placed in the UV (Type A, 315-400 nm) chamber for contact times ranging up to 24 h. After specific times of exposure to UVA irradiation, the samples were removed from the UV chamber and titrated, or rechlorinated and titrated. The temperature was 37.6° C., and the relative humidity was 17% during the UVA light irradiation. The UV chamber provided an irradiance of 0.68 W/m² at 340 nm which approximates the irradiance provided by noon summer sunlight.

Washing stabilities of the coated cotton swatches are summarized in Table 8. As expected, increasing number of washing cycles resulted a progressive decline in the chlorine loadings. The coating was remarkably durable on cotton fabric such that even after 50 machine washings, only 20% of the coating was washed away from the surfaces.

TABLE 8

Stability toward Washing of Cotton Coated with Synthesized HAOH Copolymer (Cl⁺ % Remaining).

| MW[a] | C[b] | R[b] | U[b] |
|---|---|---|---|
| 0 | 0.35 | | |
| 5 | 0.15 | 0.32 | 0.32 |
| 10 | 0.14 | 0.32 | 0.31 |
| 25 | 0.11 | 0.31 | 0.30 |
| 50 | 0.06 | 0.31 | 0.29 |

[a]MW: Machine washes,
[b]C: Chlorinated before washing, R: Chlorinated before washing and rechlorinated after washing, U: Unchlorinated before washing, but chlorinated after washing, The error in the measured Cl⁺ weight percentage values was ±0.01.

Table 9 illustrates the UVA light stability of the coated cotton fabrics. UVA photons caused around 70% of the initial chlorine to be lost from the surfaces after one day of exposure. However, the swatches retained enough oxidative chlorine (0.10 Cl⁺%) for efficient biocidal efficacies. Chlorinated swatches were rechlorinated at 24 h UVA exposure intervals. After the third rechlorination (72 h exposed), 60% photolytic decomposition was obtained. This decomposition is probably due to cleavage of the ester bonds present in the coating. The unchlorinated swatches did not exhibit a significant decomposition.

TABLE 9

Stability toward UVA Light of Cotton Coated with Synthesized HAOH Copolymer (Cl⁺ % Remaining).

| Time (h) | Chlorinated | Unchlorinated |
|---|---|---|
| 0 | 0.32 | |
| 1 | 0.27 | |
| 2 | 0.24 | |
| 3 | 0.17 | |
| 6 | 0.16 | |
| 12 | 0.13 | |
| 24 | 0.10 | |
| 24R₁[a] | 0.31 | 0.32 |
| 48 | 0.08 | |
| 48R₂ | 0.24 | 0.31 |
| 72 | 0.06 | |
| 72R₃ | 0.13 | 0.29 |

[a]R₁ to R₃ indicate rechlorination of samples after UVA exposure for the specified time intervals. The error in the measured Cl⁺ weight percentage values was ±0.01.

Example 14

Biocidal Testing of Copolymer HASL Coated on Cotton

A "sandwich test" was used to evaluate biocidal efficacy. Both chlorinated and unchlorinated coated cotton samples were challenged with *Staphylococcus aureus* (ATCC 6538) and *Escherichia coli* O157:H7 (ATCC 43895) bacterial suspensions in pH 7 phosphate buffer solution (100 mM). Suspensions (25 μl) of the bacterial solution (about 10⁸ CFU (colony-forming units)) were added to the center of a 2.54 cm square fabric swatch, and a second identical swatch was placed on top of the first swatch. A sterile weight was used to ensure sufficient contact of the swatches with the inocula. The contact times for the bacteria with the swatches were 1, 5, 10, and 30 min. At those contact times the fabric swatches were quenched with 0.02 N sodium thiosulfate solution to remove any oxidative chlorine which could cause extended disinfection. Organisms were removed from the fabric by vigorous vortex mixing after which serial dilutions of the solutions contacting the surfaces were plated on Trypticase agar, incubated for 24 h at 37° C., and colony counts were made to determine the presence or absence of viable bacteria. Unchlorinated control samples were treated in the same manner.

The results are shown in Table 10. The unchlorinated control samples (11) provided only about 0.10 log reductions, due to the adhesion of bacteria to the cotton swatches, within 30 min contact time intervals. All of the chlorinated coated samples (11-Cl) with chlorine loadings of 0.23-0.24 wt % showed excellent biocidal activity. 11-Cl inactivated all *S. aureus* with log reduction of ca. 8.2 in a contact time of 10 min and 5 min, in Exp1 and Exp2, respectively. A small degree of inconsistency was found in the repeated experiment. When the experiment was run a third time, a complete 7.98 log reduction was obtained at the 5 min contact time. This is probably due to the difficulty of performing reproducible bacterial testing on surfaces of textiles. On the other hand, 11-Cl inactivated all *E. coli* O157:H7 with log reduction of around 8.2 in a contact time of 5 min in repeated experiments. It is notable that a sample of 15-Cl containing a chlorine loading of only 0.10 wt % produced complete log reductions of 7.98 and 8.01 for *S. aureus* and *E. coli* O157:H7, respectively, at contact times of both 5 and 10 min.

TABLE 10

Biocidal Tests (Log Reduction).

| | Contact time | Exp1[a] | | Exp2[b] | |
|---|---|---|---|---|---|
| Sample | (min) | S. aureus | E. coli | S. aureus | E. coli |
| 11 (control) | 30 | 0.05 | 0.02 | 0.04 | 0.11 |
| 11-Cl | 1 | 4.13 | 5.46 | 4.07 | 5.86 |
| | 5 | 4.22[c] | 8.18 | 8.24 | 8.16 |
| | 10 | 8.16 | 8.18 | 8.24 | 8.16 |
| | 30 | 8.16 | 8.18 | 8.24 | 8.16 |

[a]Exp 1: The inoculum concentrations were 8.16, and 8.18 logs for *S. aureus*, and *E. coli*, respectively. Chlorine loading on 11-Cl was 0.24 wt %.
[b]Exp 2: The inoculum concentrations were 8.24, and 8.16 logs for *S. aureus*, and *E. coli*, respectively. Chlorine loading on 11-Cl was 0.25 wt %.
[c]In a third experiment a total inactivation of 7.98 logs was obtained for an inoculum concentration of 7.98 logs at a chlorine loading of 0.24 wt %.

Thus, the copolymer chlorinated HASL functions very well as a biocidal coating on cotton fibers.

Example 15

Biocidal Testing of Copolymer HASA in Latex Paint

A "sandwich test" was used to evaluate the biocidal efficacies. Both chlorinated and unchlorinated paint samples (coated polyester transparency slides) were challenged with *S. aureus* (ATCC 6538) and *E. coli* O157:H7 (ATCC 43895) bacterial suspensions in pH 7 phosphate buffer solution (100 mM). The bacteria purchased from the American Type Culture Collection (Rockville, Md.) were stored at −80° C. in 10% dimethylsulfoxide trypticase soy broth (Difco Laboratories, Detroit Mich.) before use. Suspensions (25 μl) of the bacterial solution (6-7 logs concentration) were added to the center of a 2.54 cm square paint sample, and a second identical sample was placed on top of the first one. The contact times for the bacteria with the samples were 5 and 10 min. At those contact times the paint samples were quenched with 0.02 N sodium thiosulfate solution to remove any oxidative chlorine which could cause extended disinfection. Organisms were removed from the fabric by vigorous vortex mixing after which serial dilutions of the solutions contacting the surfaces were plated on Trypticase agar, incubated for 24 h at 37° C., and colony counts were made to determine the presence or absence of viable bacteria. Unchlorinated control samples were treated in the same manner.

The treated paint samples were stored for 10 d to remove the non-covalently bonded, occluded chlorine from the paint matrix before the bacterial challenges were performed. The challenge concentrations were about $10^7$ CFU (colony-forming units) for both bacteria. The results are presented in Table 11. The control samples, chlorinated paint sample (Paint-Cl), and unchlorinated polymers (10, 9, 8, and 7) provided only about 0.10 log reductions, due to the adhesion of bacteria to the paint samples, within 10 min of contact time. Thus, the in-can paint preservatives in the latex paint provided little, if any, biocidal activity. It is of interest that the chlorinated homopolymer sample (10-Cl) also did not provide any biocidal property. This was probably due to the insufficient contact of microorganisms with the chlorine loaded polymer particles, which could not be dispersed uniformly in the paint. Because the mechanism of biocidal action of N-halamines is the direct transfer of oxidative halogen to microbial cells, spaces among the aggregates of 10-Cl in the paint had no direct contact of the polymer with the bacteria resulting in undetectable biocidal action. On the other hand, copolymers 9, 8, and 7, which were dispersible/soluble in the paint provided a total inactivation of both $S.$ $aureus$ and $E.$ $coli$ O157:H7 within 5 min of contact time in the repeated experiments. This observation underlines the importance of using soluble N-halamine copolymers in latex paints. Insoluble N-halamine homopolymers are not satisfactory for use with water based paints. It should be noted that in one experiment a paint sample treated with copolymer 7, tested at a chlorine loading of 0.16 wt % for biocidal efficacy, and then rechlorinated to 0.16 wt %, and retested for biocidal efficacy provided a complete inactivation (about 6.5 logs) for both bacteria. Thus, there was no decline in efficacy brought about by a rechlorination process.

TABLE 11

Biocidal Tests (Log Reduction).

| Sample/ | Contact time | Exp 1[a] | | Exp 2[b] | |
| --- | --- | --- | --- | --- | --- |
| Cl+ % | (min) | S. aureus | E. coli | S. aureus | E. coli |
| Paint-Cl | 10 | 0.18 | 0.05 | 0.14 | 0.10 |
| 10 | 10 | 0.01 | 0.01 | 0.11 | 0.09 |
| 9 | 10 | 0.09 | 0.14 | 0.06 | 0.12 |
| 8 | 10 | 0.13 | 0.01 | 0.15 | 0.04 |
| 7 | 10 | 0.02 | 0.25 | 0.13 | 0.22 |
| 10-Cl | 5 | 0.05 | 0.03 | 0.12 | 0.07 |
| 0.41 | 10 | 0.04 | 0.12 | 0.25 | 0.05 |
| 9-Cl | 5 | 6.60 | 6.52 | 6.38 | 6.24 |
| 0.28 | 10 | 6.60 | 6.52 | 6.38 | 6.24 |
| 8-Cl | 5 | 6.60 | 6.52 | 6.38 | 6.24 |
| 0.29 | 10 | 6.60 | 6.52 | 6.38 | 6.24 |
| 7-Cl | 5 | 6.60 | 6.52 | 6.38 | 6.24 |
| 0.18 | 10 | 6.60 | 6.52 | 6.38 | 6.24 |

[a]Exp 1: The inoculum concentrations were 6.60 and 6.52 logs for S. aureus and E. coli O157:H7, respectively.
[b]Exp 2: The inoculum concentrations were 6.38 and 6.24 logs for S. aureus and E. coli O157:H7, respectively.

For samples of treated and chlorinated paint exposed to lengthy periods of UVA light, excellent results were obtained upon challenges with the two species of bacteria. For example, a sample of 7-Cl exposed to UVA photons for 42 days, then rechlorinated, then exposed to UVA photons for a further period of 28 days, contained a chlorine loading of 0.11 wt %, but it still provided complete inactivation of both bacteria (6.2-6.4 logs) within 5 min. It can be concluded that copolymer HASA, when added to a latex paint and then chlorinated, provides excellent biocidal efficacy for the coated surface even in the presence of ambient and ultraviolet light.

Example 16

Biocidal Testing of Copolymer HAGM Coated on Cotton

A "sandwich test" was used to evaluate the biocidal efficacy. Both chlorinated and unchlorinated coated cotton samples were challenged with *Staphylococcus aureus* (ATCC 6538) and *Escherichia coli* O157:H7 (ATCC 43895) bacterial suspensions in pH 7 phosphate buffer solution (100 mM). Suspensions (25 μl) of the bacterial solution (about $10^6$ CFU (colony-forming units)) were added to the center of a 2.54 cm square fabric swatch, and a second identical swatch was placed on top of the first swatch. A sterile weight was used to ensure sufficient contact of the swatches with the inocula. The contact times for the bacteria with the swatches were 2, 5, and 10 min. At those contact times the fabric swatches were quenched with 0.02 N sodium thiosulfate solution to remove any oxidative chlorine that could cause extended disinfection. Organisms were removed from the fabric by vigorous vortex mixing after which serial dilutions of the solutions contacting the surfaces were plated on Trypticase agar, incubated for 24 h at 37° C., and colony counts were made to determine the presence or absence of viable bacteria. Unchlorinated control samples were treated in the same manner.

The results are shown in Table 12. The unchlorinated control samples did not exhibit significant biocidal efficacies. The limited bacteria reduction that the control samples provided is due to the adhesion of bacteria to the cotton swatches. On the other hand, the chlorinated samples effectively inactivated the microorganisms within remarkably brief contact times. In the first experiment, the chlorinated samples exhibited a total inactivation of Gram-positive and Gram-negative bacteria within 2 and 5 min of contact time, respectively. On the other hand, when the test was repeated, 2 min was sufficient for complete inactivation of both types of bacteria. This lack of reproducibility was probably due to the difficulty of performing reproducible bacterial testing on surfaces of textiles or the differences in chlorine loadings of the swatches used. It is well known that increasing chlorine loading increases the hydrophobicity of the surfaces, which can result in poor contact with bacteria.

TABLE 12

Biocidal Tests of Cotton Coated with Synthesized HAGMCopolymer.

| | Contact time (min) | Exp1[a] | | Exp2[b] | |
| --- | --- | --- | --- | --- | --- |
| Sample | (min) | S. aureus | E. coli | S. aureus | E. coli |
| Control | 10 | 0.27 | 0.09 | 0.21 | 0.03 |
| Chlorinated | 2 | 6.57 | 3.61 | 6.52 | 6.24 |
| | 5 | 6.57 | 6.55 | 6.52 | 6.24 |
| | 10 | 6.57 | 6.55 | 6.52 | 6.24 |

[a]Exp 1: The inoculum concentrations were 6.57 and 6.55 logs for S. aureus and E. coli, respectively. Chlorine loading of the swatches was 0.36 wt %.
[b]Exp 2: The inoculum concentrations were 6.52 and 6.24 logs for S. aureus and E. coli, respectively. Chlorine loading of the swatches was 0.26 wt %.

Thus, the copolymer chlorinated HAGM functions superbly as a biocidal coating on cotton fibers.

Example 17

Biocidal Testing of Copolymer HAOH Coated on Cotton

A "sandwich test" was used to evaluate the biocidal efficacy. Both chlorinated and unchlorinated coated cotton samples were challenged with *Staphylococcus aureus* (ATCC 6538) and *Escherichia coli* O157:H7 (ATCC 43895) bacterial suspensions in pH 7 phosphate buffer solution (100 mM). Suspensions (25 μl) of the bacterial solution (about $10^6$ CFU (colony-forming units)) were added to the center of a 2.54 cm square fabric swatch, and a second identical swatch was placed on top of the first swatch. A sterile weight was used to ensure sufficient contact of the swatches with the inocula. The contact times for the bacteria with the swatches were 2, 5, and 10 min. At those contact times the fabric swatches were quenched with 0.02 N sodium thiosulfate solution to remove any oxidative chlorine which could cause extended disinfection. Organisms were removed from the fabric by vigorous vortex mixing after which serial dilutions of the solutions contacting the surfaces were plated on Trypticase agar, incubated for 24 h at 37° C., and colony counts were made to determine the presence or absence of viable bacteria. Unchlorinated control samples were treated in the same manner.

The results are shown in Table 13. The chlorinated swatches exhibited complete inactivation of Gram-positive and Gram-negative bacteria within 2 min of contact time. However, the unchlorinated control swatches did not exhibit significant biocidal efficacy even for the longest contact time. The limited reduction that the control samples provided is due the adhesion of the bacteria to the cotton surface.

TABLE 13

Biocidal Tests of Cotton Coated with Synthesized HAOH Copolymer

| Sample | Contact time (min) | Exp1[a] S. aureus | E. coli | Exp2[b] S. aureus | E. coli |
|---|---|---|---|---|---|
| Control | 10 | 0.17 | 0.12 | 0.29 | 0.02 |
| Chlorinated | 2 | 6.57 | 6.55 | 6.52 | 6.24 |
|  | 5 | 6.57 | 6.55 | 6.52 | 6.24 |
|  | 10 | 6.57 | 6.55 | 6.52 | 6.24 |

[a]Exp 1: The inoculum concentrations were 6.57 and 6.55 logs for *S. aureus* and *E. coli*, respectively. Chlorine loading of the swatches was 0.35 wt %.
[b]Exp 2: The inoculum concentrations were 6.52 and 6.24 logs for *S. aureus* and *E. coli*, respectively. Chlorine loading of the swatches was 0.28 wt %.

Thus, the copolymer chlorinated HAOH functions superbly as a biocidal coating on cotton fibers.

Example 18

Biocidal Filter Media

A stock solution of copolymer HASA 7 was prepared at 5 wt % in water. To 8 g of the stock solution were added 10 g of water and 2 g of household bleach (6% sodium hypochlorite). The concentration of the copolymer in the final solution was 2 wt %. The pH was measured to be 10.8 and was reduced to pH 7.1 by adding 12 drops of 6 M HCl during the chlorination process. Commercial filter media swatches reported to be derived from nanometer sized fibers of aluminum hydroxide combined with fine glass fibers, refined cellulose fibers, and possibly other synthetic fibers (see U.S. Pat. No. 7,390,343 B2 and U.S. Pat. No. 7,311,752 B2) were obtained from Argonide Corporation (Sanford, Fla.). The filter swatches were immersed into the copolymer solution for one min and then removed and held at 125° C. for 15 min, followed by an additional one hour at 45° C. The oxidative chlorine loading on the treated swatch determined by iodometric/thiosulfate titration was 0.42 wt %. This chlorine loading would be biocidal (see data for HASA 7-Cl in Example 15) in an air filter application.

Example 19

The Chlorine Loading of Monomer HA

The Chlorine Loading of Monomer HA (3 g) was determined by adding into a solution of 36 mL water, 4 mL of bleach (6% sodium hypochlorite), and 1.25 g of sodium bicarbonate. The mixture was stirred for 2 h, and the insoluble white particles were removed by filtration. The product was vigorously washed with distilled water and dried at 45° C. for 1 h. The chlorine loading on the particles (HA-Cl) determined by iodometric/thiosulfate titration was measured to be 30.77 wt %; the theoretical value for the trichlorinated structure is 31.09 wt %. Its structure was further confirmed by NMR and FTIR spectroscopies.

Example 20

The Bromine Loading of Monomer HA

HA (1.8 g) was dissolved in a solution of 50 mL of 2 N NaOH. While stirring the solution, 2 g of liquid bromine were added dropwise at room temperature. The pH was adjusted to 8.0 with 4 N acetic acid, and the mixture was stirred for 1 h at room temperature. The insoluble product was recovered by filtration, washed with distilled water, and dried in air at room temperature for 4 h. The bromine loading on the particles determined by iodometric/thiosulfate titration was measured to be 27.76 wt %; the theoretical value for the tribrominated structure is 50.36 wt %. The procedure was not optimized to obtain higher bromine loading.

Throughout this application, various publications are referenced. The disclosures of these publications in their entireties are hereby incorporated by reference in this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed is:

1. A compound having the structure

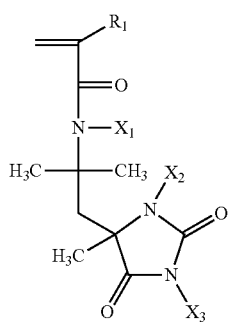

wherein, $R_1$ is H or methyl, and $X_1$, $X_2$, and $X_3$ are independently H, Cl, or Br.

2. The compound of claim 1, wherein no more than two of $X_1$, $X_2$, and $X_3$ are H.

3. A homopolymer comprising the polymerization product of the compound of claim 1.

4. The homopolymer of claim 3, wherein no more than two of $X_1$, $X_2$, and $X_3$ are H.

5. A copolymer having the structure

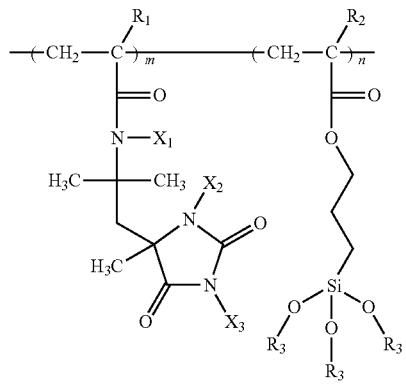

wherein, $R_1$ and $R_2$ are independently H or methyl, and $X_1$, $X_2$, and $X_3$ are independently H, Cl, or Br; $R_3$ is H, methyl, or ethyl; and the ratio of the coefficients m to m+n is between 0.99 and 0.01.

6. The copolymer of claim 5, wherein no more than two of $X_1$, $X_2$, and $X_3$ are H.

7. The copolymer of claim 5, wherein the ratio of the coefficients m to m+n is between 0.6 to 0.4.

8. The copolymer of claim 7, wherein no more than two of $X_1$, $X_2$, and $X_3$ are H.

9. A copolymer having the structure

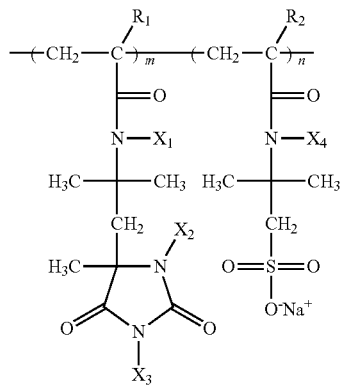

wherein, $R_1$ and $R_2$ are independently H or methyl; $X_1$, $X_2$, $X_3$, and $X_4$ are independently H, Cl, or Br; and the ratio of the coefficients m to m+n is between 0.99 and 0.01.

10. The copolymer of claim 9, wherein no more than three of $X_1$, $X_2$, $X_3$, and $X_4$ are H.

11. The copolymer of claim 9, wherein the ratio of the coefficients m to m+n is between 0.8 to 0.7.

12. The copolymer of claim 11, wherein no more than three of $X_1$, $X_2$, $X_3$, and $X_4$ are H.

13. The copolymer having the structure

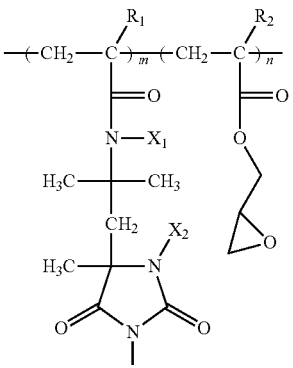

wherein, $R_1$ and $R_2$ are independently H or methyl; $X_1$, $X_2$, and $X_3$ are independently H, Cl, or Br; and the ratio of the coefficients m to m+n is between 0.99 and 0.01.

14. The copolymer of claim 13, wherein no more than two of $X_1$, $X_2$, and $X_3$ are H.

15. The copolymer of claim 13, wherein the ratio of the coefficients m to m+n is between 0.6 to 0.4.

16. The copolymer of claim 15, wherein no more than two of $X_1$, $X_2$, and $X_3$ are H.

17. A copolymer having the structure

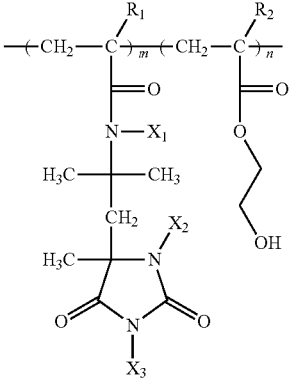

wherein, $R_1$ and $R_2$ are independently H or methyl; $X_1$, $X_2$, and $X_3$ are independently H, Cl, or Br; and the ratio of the coefficients m to m+n is between 0.99 and 0.01.

18. The copolymer of claim 17, wherein no more than two of $X_1$, $X_2$, and $X_3$ are H.

19. The copolymer of claim 17, wherein the ratio of the coefficients m to m+n is between 0.6 to 0.4.

20. The copolymer of claim 19, wherein no more than two of $X_1$, $X_2$, and $X_3$ are H.

21. A mixture comprising the compound of claim 9 and latex paint.

22. An article comprising the compound of claim 1 attached to a surface of cellulose, synthetic fibers, filter materials, chitin, glass, ceramics, plastics, rubber, porcelain, acrylic films, silicon tubing, marble, metal oxides, and silica, or mixtures thereof.

23. An article comprising the copolymer of claim 5 attached to a surface of cellulose, synthetic fibers, filter materials, chitin, glass, ceramics, plastics, rubber, porcelain, acrylic films, silicon tubing, marble, metal oxides, and silica, or mixtures thereof.

24. An article comprising the copolymer of claim 9 attached to a surface of cellulose, synthetic fibers, filter materials, chitin, glass, ceramics, plastics, rubber, porcelain, acrylic films, silicon tubing, marble, metal oxides, and silica, or mixtures thereof.

25. An article comprising the copolymer of claim 13 attached to a surface of cellulose, synthetic fibers, filter materials, chitin, glass, ceramics, plastics, rubber, porcelain, acrylic films, silicon tubing, marble, metal oxides, and silica, or mixtures thereof.

26. An article comprising the copolymer of claim 17 attached to a surface of cellulose, synthetic fibers, filter materials, chitin, glass, ceramics, plastics, rubber, porcelain, acrylic films, silicon tubing, marble, metal oxides, and silica, or mixtures thereof.

27. A method comprising exposing the compound of claim 1 to a source of oxidative chlorine or bromine.

28. A method comprising exposing the compound of claim 5 to a source of oxidative chlorine or bromine.

29. A method comprising exposing the compound of claim 9 to a source of oxidative chlorine or bromine.

30. A method comprising exposing the compound of claim 13 to a source of oxidative chlorine or bromine.

31. A method comprising exposing the compound of claim 17 to a source of oxidative chlorine or bromine.

32. A method comprising covalently bonding the compound of claim 1 to pendent OH groups of a substrate.

33. A substrate coated with the compound of claim 1.

34. A substrate having the compound of claim 1 attached thereto.

35. A method of inactivating bacteria, fungi or virus particles comprising containing the bacteria, fungi or virus particles with the compound of claim 1.

36. A method of inactivating bacteria, fungi or virus particles comprising contacting the bacteria, fungi or virus particles with the copolymer of claim 5.

37. A method of inactivating bacteria, fungi or virus particles comprising contacting the bacteria, fungi or virus particles with the copolymer of claim 9.

38. A method of inactivating bacteria, fungi or virus particles comprising contacting the bacteria, fungi or virus particles with the copolymer of claim 13.

39. A method of inactivating bacteria, fungi or virus particles comprising contacting the bacteria, fungi or virus particles with the copolymer of claim 17.

40. A method comprising:
attaching the compound of claim 1 to a surface of an article; and
exposing the compound of claim 1 on the surface to a source of oxidative chlorine or bromine.

41. A method comprising:
attaching the compound of claim 5 to a surface of an article; and
exposing the compound of claim 5 on the surface to a source of oxidative chlorine or bromine.

42. A method comprising:
attaching a non-halogenated compound of claim 9 to a surface of an article; and
exposing the compound of claim 9 on the surface to a source of oxidative chlorine or bromine.

43. A method comprising:
attaching a non-halogenated compound of claim 13 to a surface of an article; and
exposing the compound of claim 13 on the surface to a source of oxidative chlorine or bromine.

44. A method comprising:
attaching a non-halogenated compound of claim 17 to a surface of an article; and
exposing the compound of claim 17 on the surface to a source of oxidative chlorine or bromine.

* * * * *

UNITED STATES PATENT AND TRADEMARK OFFICE
CERTIFICATE OF CORRECTION

PATENT NO. : 8,496,920 B2  Page 1 of 1
APPLICATION NO. : 13/270446
DATED : July 30, 2013
INVENTOR(S) : Shelby D. Worley et al.

It is certified that error appears in the above-identified patent and that said Letters Patent is hereby corrected as shown below:

In the Claims:

At Column 35, Claim 35, Line 32: "comprising containing the bacteria" should read -- comprising contacting the bacteria --

Signed and Sealed this
Fourth Day of August, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO. : 8,496,920 B2
APPLICATION NO. : 13/270446
DATED : July 30, 2013
INVENTOR(S) : Shelby D. Worley et al.

It is certified that error appears in the above-identified patent and that said Letters Patent is hereby corrected as shown below:

In the Specification

Column 1, Line 11, insert:
--GOVERNMENT SUPPORT CLAUSE
This invention was made with Government support under ITA-06-3112 awarded by the United States Department of Commerce and F08637-02-C-7020 awarded by the United State Air Force. The Government has certain rights in the invention.--

Signed and Sealed this
First Day of June, 2021

Drew Hirshfeld
*Performing the Functions and Duties of the
Under Secretary of Commerce for Intellectual Property and
Director of the United States Patent and Trademark Office*